(12) United States Patent
Dattwyler et al.

(10) Patent No.: US 7,887,815 B2
(45) Date of Patent: Feb. 15, 2011

(54) PEPTIDE DIAGNOSTIC AGENT FOR LYME DISEASE

(75) Inventors: Raymond J. Dattwyler, East Setauket, NY (US); Maria Gomes-Solecki, Memphis, TN (US)

(73) Assignee: Biopeptides Corporation, East Setauket, NY (US)

( * ) Notice: Subject to any disclaimer, the term of this patent is extended or adjusted under 35 U.S.C. 154(b) by 0 days.

(21) Appl. No.: 12/292,044

(22) Filed: Nov. 10, 2008

(65) Prior Publication Data

US 2009/0162875 A1    Jun. 25, 2009

Related U.S. Application Data

(63) Continuation-in-part of application No. PCT/US2007/011289, filed on May 10, 2007.

(60) Provisional application No. 60/799,016, filed on May 10, 2006, provisional application No. 60/875,820, filed on Dec. 20, 2006.

(51) Int. Cl.
*A61K 39/00* (2006.01)
*A61K 39/02* (2006.01)
*A61K 38/00* (2006.01)
*C12Q 1/00* (2006.01)
*G01N 33/53* (2006.01)
*G01N 33/554* (2006.01)

(52) U.S. Cl. .................. 424/234.1; 424/184.1; 435/4; 435/7.1; 435/7.3; 435/7.32; 530/300; 530/324

(58) Field of Classification Search ................. None
See application file for complete search history.

(56) References Cited

U.S. PATENT DOCUMENTS

| | | |
|---|---|---|
| 5,618,533 A | 4/1997 | Flavell et al. |
| 6,437,116 B1 | 8/2002 | Norris et al. |
| 6,475,492 B1 | 11/2002 | Phillipp et al. |
| 6,660,274 B2 | 12/2003 | Phillipp et al. |
| 6,719,983 B2 | 4/2004 | Norris et al. |
| 6,740,744 B2 | 5/2004 | Norris et al. |
| 6,878,816 B2 | 4/2005 | Norris et al. |
| 7,135,176 B2 | 11/2006 | Norris et al. |
| 2003/0129680 A1 | 7/2003 | O'Connor, Jr. |

FOREIGN PATENT DOCUMENTS

WO    WO 00/65054    11/2000

OTHER PUBLICATIONS

Gomes-Solecki, Journal of Clinical Microbiological, vol. 28, No. Jul. 2000, p. 2530-2535.*
Liang et al, Infection and Immunity, Apr. 2000, vol. 68, No. 4, p. 2349-2352.*
Liang et al, The Journal of Immunology, 1999, 163, 5566-5573.*
International Search Report/Written Opinion.
Lyme Borreliosis, Poster presented by M. Gomes-Solecki at a conference in Helsinki, Sweden, May 10-12, 2006.
Centers for Disease Control and Prevention. Recommendations for test performance and interpretation from the Second National Conference on Serologic Diagnosis of Lyme Disease. MMWR; 44:590-591. 1995.
Engstrom SM, Shoop E, Johnson RC. Immunoblot interpretation criteria for serodiagnosis of early Lyme disease. J Clin Microbiol. ;33(2):419-27. 1995.
Bacon RM, Biggerstaff BJ, Schriefer ME, Gilmore RD Jr, Philipp MT, Steere AC, Wormser GP, Marques AR, Johnson BJ. Serodiagnosis of Lyme disease by kinetic enzyme-linked immunosorbent assay using recombinant V1sE1 or peptide antigens of Borrelia burgdorferi compared with 2-tiered testing using whole-cell lysates. J Infect Dis. Apr. 15, 2003;187(8):1187-99.
Iyer, R; Hardham, JM; Wormser, GP; Schwartz, I; and Norris, SJ. Conservation and Heterogeneity of VlsE among Human and Tick Isolates of *Borrelia burgdorferi*. Infect. Immun. 68: 714-8, 2000.
Lawrenz MB, Hardham JM, Owens RT, et al. Human antibody responses to VlsE antigenic variation protein of *Borrelia burgdorferi*. J Clin Microbiol; 37:3997-4004. 1999.
Liang FT, Alvarez AL, Gu Y, Nowling JM, Ramamoorthy R, Philipp MT. An immunodominant conserved region within the variable domain of VlsE, the variable surface antigen of *Borrelia burgdorferi*. J Immunol; 163:5566-73. 1999.
Liang FT, Steere AC, Marques AR, Johnson BJ, Miller JN, Philipp MT. Sensitive and specific serodiagnosis of Lyme disease by enzyme-linked immunosorbent assay with a peptide based on an immunodominant conserved region of *Borrelia burgdorferi*vlsE. J Clin Microbiol.; 37(12):3990-6. 1999.
Liang FT, Philipp MT. Epitope mapping of the immunodominant invariable region of *Borrelia burgdorferi* VlsE in three host species. Infect Immun.; 68(4):2349-52. 2000.
Sillanpaa, H., P. Lahdenne, H. Sarvas, M. Arnez, A. Steere, M. Peltomaa, and I. Seppala. 2007. Immune responses to borrelial VlsE IR6 peptide variants. Int J Med Microbiol 297:45-52.
Smismans, A., V. J. Goossens, E. Nulens, and C. A. Bruggeman. 2006. Comparison of five different immunoassays for the detection of *Borrelia burgdorferi* IgM and IgG antibodies. Clin Microbiol Infect 12:648-55.

* cited by examiner

*Primary Examiner*—Vanessa L. Ford
(74) *Attorney, Agent, or Firm*—Venable LLP; Nancy J. Axelrod; Ann S. Hobbs

(57) ABSTRACT

The present invention relates, e.g., to an isolated peptide consisting of the sequence MKKDDQIAAAIALRGMA (SEQ ID NO:1) or an active variant thereof, wherein the peptide or active variant can bind specifically to an antibody induced by a causative agent of Lyme disease (a pathogenic *Borrelia*), e.g. in a sample from a subject having Lyme disease. Also disclosed are linear multimeric peptides that contain the peptide represented by SEQ ID NO:1 as well as one or more additional peptide epitopes from other *Borrelia* proteins that can also bind specifically to an antibody as above. Compositions and diagnostic kits comprising a peptide of the invention are described, as are diagnostic assays using the peptide(s).

21 Claims, 1 Drawing Sheet

PEPTIDE DIAGNOSTIC AGENT FOR LYME DISEASE

This application claims the benefit of U.S. provisional applications 60/779,016, filed May 10, 2006 and 60/875,820, filed Dec. 20, 2006, and is a CIP of PCT/US2007/011289, filed May 10, 2007, all of which are incorporated by reference herein in their entirety.

This application was made with U.S. government support (NIH-NIAID, grant number R43AI074092). Therefore, the government has certain rights in the invention.

FIELD OF THE INVENTION

This invention relates, e.g., to agents and methods for diagnosing Lyme disease.

BACKGROUND INFORMATION

Lyme disease (sometimes referred to herein as LD or Lyme borreliosis) is a common vector-borne disease that is a significant public health concern. The disease is transmitted by the bite of various species of *Ixodes* ticks carrying the etiologic agent, a pathogenic *Borrelia* bacterium (a spirochete). Organisms of the *Borrelia burgdorferi* sensu lato group belong to the family *Spirochaetaceae*, genus *Borrelia*. There are at least 11 species in the *B. burgdorferi* complex and an unknown but large number of substrains. At least three genospecies of the *Borrelia burgdorferi* sensu lato group have been identified as pathogens: *B. burgdorferi* sensu stricto, *B. afzelii*, and *B. garinii*. In addition, other species of *Borrelia* have been implicated as being causative pathogenic agents. The major reservoir of the infection in the United States is the white footed mouse, and the infection can be transmitted to many mammalian species, including various other forms of wildlife, e.g. Eastern chipmunks, and dogs, cats, and humans.

Clinically, Lyme disease is a progressive disease with a wide array of manifestations. Early diagnosis and treatment is critical to prevent progression. Late disseminated infection can be associated with permanent damage to the nervous and musculoskeletal systems. Unlike most bacterial diseases that can be defined microbiologically by direct observation or culture of the pathogen, *B. burgdorferi* is difficult to culture or observe in clinical samples. Therefore, Lyme disease is defined indirectly. Erythema migrans (EM) is the classic marker for this infection at early stages. However, not all patients infected with pathogenic *Borrelia* develop EM. In the absence of EM, the current basis for diagnosis is the demonstration of an antibody response against a pathogenic *Borrelia* in an appropriate clinical setting.

Unfortunately, current serologic assays for such antibodies suffer from both low sensitivity and specificity, especially in early disease. The U.S. Centers for Disease Control and Prevention (CDC) currently recommends that in order for a patient to be considered seropositive, two assays must be positive: a first tier assay, such as an ELISA, IFA or lateral flow assay, followed by a second tier assay, such as a western blot. This approach is expensive and can delay diagnosis for a week or more, but it is necessary because of the poor specificity of the most commonly used first tier assays. There is a need for a simple, sensitive and specific diagnostic method for the detection of Lyme disease, particularly at early times after infection.

A peptide-based immunodiagnostic assay has been developed and approved by the FDA for use in the United States as a first tier assay. This test is based on the presence in a subject of antibodies to an immunodominant region (IR6) from the *B. burgdorferi* surface antigen, VlsE (VMP like sequence expressed), which is present in all three known pathogenic genospecies. The assay is described, e.g., in U.S. Pat. No. 6,475,492. The sequence of the peptide used in the approved assay, a 26 amino acid peptide derived from the European pathogenic *Borrelai* species, *B garinii*, is CMKKDDQIAAAMVLRGMAKDGQFALK (SEQ ID NO:2). An epitope mapping analysis of this peptide by the inventors of that patent (Liang et al. (2000) Infect Immun. 68, 2349-2353) concludes that, at least in monkeys and humans, this amino acid sequence is recognized as a single antigenic determinant.

The present inventors have identified a shorter version of the 26 amino acid IR6 peptide, which may contain certain amino acid substitutions, that provides the basis for a sensitive and specific immunoassay for Lyme disease.

DESCRIPTION OF THE INVENTION

Figure 1:
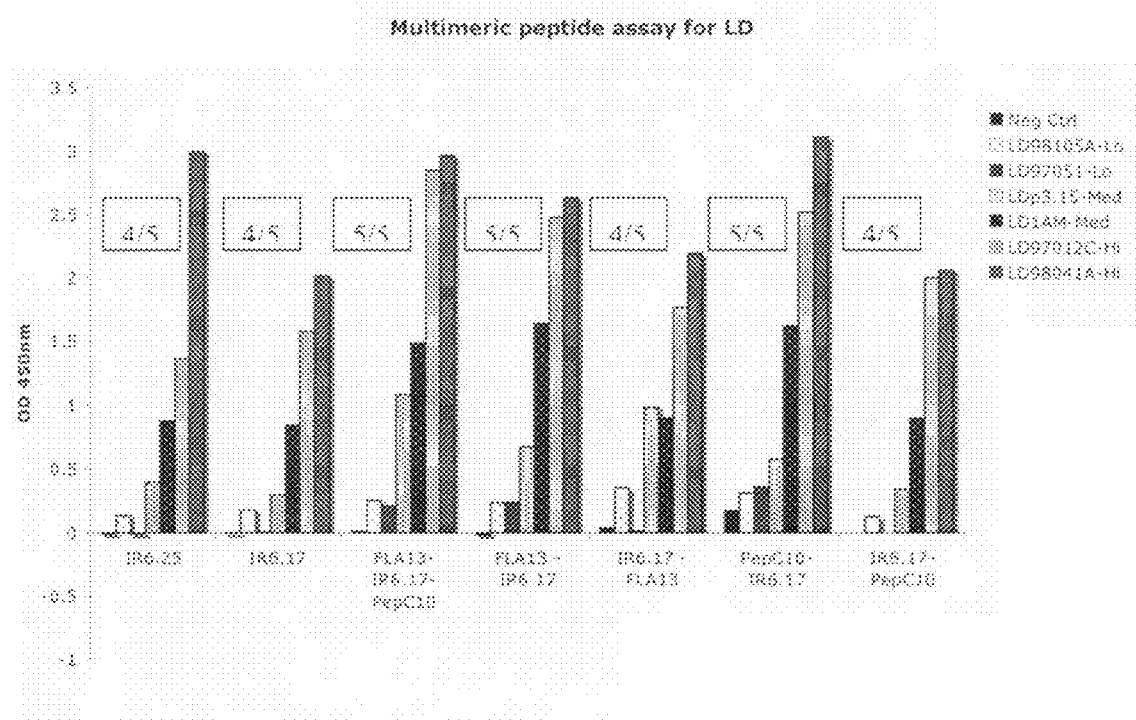
FIG. 1 shows a comparison between multimeric IR6 based peptide assays and standards based on single IR6 peptides (-25 and -17 residues) for detection of anti-*Borrelia* antibodies in sera from Lyme disease patients. Different combinations of multimeric peptides based on three *B. burgdorferi* antigens (Fla-p41, VlsE-IR6 and OspC) detected anti-*B. burgdorferi* antibodies with higher sensitivity than the single based IR6 peptides. LD98105A and LD97051 are Lyme disease samples with a low titer of anti-*B. burgdorferi* antibodies; LDp3.15 and LD1AM are Lyme disease samples with a medium titer of anti-*B. burgdorferi* antibodies; LD7012C and LD98041A are Lyme disease samples with a high titer of anti-*B. burgdorferi* antibodies; Neg Ctrl is a negative control, a serum sample from a healthy individual.

The present inventors, by using a finely detailed mapping strategy, have found, surprisingly, that a peptide which is shortened from both the N-terminal and the C-terminal ends of the 26 amino acid IR6 peptide can specifically and efficiently recognize antibodies to a pathogenic *Borrelia* that develop in a subject infected with a pathogen from the *Borrelia burgdorferi* sensu lato group. The shortened peptide identified by the inventors was derived from the IR6 region of a North American pathogenic species of *B. burgdorferi*, *B. burgdorferi* sensu stricto. The peptide identified by the inventors has the 17 amino sequence (utilizing standard single letter amino acid codes), MKKDDQIAAAIALRGMA (SEQ ID NO:1). Active variants of the peptide represented by SEQ ID NO:1 are also included in the invention. Such active variants include, e.g., peptides in which one or more of D4, I11 or A 12 is substituted with a conservative amino acid replacement. A 17 amino acid peptide from *B garinii* corresponding to this IR6 region has the sequence MKKDDQIAAAMVLRGMA (SEQ ID NO:6), which differs from SEQ ID NO:1 by two amino acids, at positions 11 and 12. Thus, the SEQ ID NO:6 peptide derived from *B garinii* is an active variant of the peptide of SEQ ID NO:1. The term "a peptide of the invention," as used herein, refers to a peptide represented by SEQ ID NO:1, or an active variant thereof.

The inventors have also found, unexpectedly, that one can generate variant peptides in which, in addition to, or instead of, substituting one or more of residues D4, I11 and/or A12 with a conservative amino acid, as discussed above, one can substitute one or more of residues Q6, A8, M16 and/or A17 with an amino acid (e.g., a conservative amino acid), and the modified peptide functions in an assay for antibodies induced by pathogenic *Borrelia* at least as well as the peptide of SEQ ID NO:1. In fact, unexpectedly, the modified peptides can detect antibodies generated against a wider range of pathogenic *B. burgdorferi* species than can be detected with a peptide (e.g., a naturally occurring peptide) from a single *Borrelia* species.

For example, the commercially available 26 amino acid peptide which contains sequences of *B. garinii* (the IP90 peptide, SEQ ID NO:2) or an 18-mer peptide from part of this sequence, interacts preferentially with sera generated in response to infection with *B. garinii*; and the peptide which contains sequences from *B. sensu stricto* (the 18-mer sequence, B31, represented by SEQ ID NO:1) reacts preferentially with sera generated in response to infection with *B. sensu* stricto. By contrast, at least some of the peptides which comprise substitutions of one or more of residues Q6, A8, M16 and/or A17 react with a variety of pathogenic *Borrelia* species. See, e.g., Example XI, which shows that at least peptides represented by SEQ ID NO:53 and 55 can recognize antibodies generated against a variety of *Borrelia* strains found in infected European populations of humans (e.g., *B. burgdorferi sensu stricto, B. garinii, B. afzelli*, and others, such as *B. lusitaniae* and *B. valaisianae*, as well as variants of any of these species), whereas peptides such as IP90 and B31, which contain naturally occurring sequences from a single *Borrelia* species, can only recognize a smaller number of *Borrelia* strains, presumably the strains corresponding to the peptides, themselves. This broader sensitivity provides a more useful agent, which can be used to detect a broader spectrum of species of pathogenic *Borrelia*.

In one embodiment of the invention, the peptide is M K K (D, N, S or R) D (Q or K) I (A, G or V) A A (M or I) (A or V) L R G (M or V) (A, G or V) (SEQ ID NO:39). In one embodiment, the residue at position 4 is N. Representative peptides of the invention include, e.g.:

```
MKKNDQIAAAIVLRGMA    (SEQ ID NO: 40)

MKKRNDNIAAAIVLRGVA   (B. afzelii p5, #89,
                     SEQ ID NO: 41)

MKKNDKIAAAIALRGMV    (#84, SEQ ID NO: 42)

MKKNDKIVAAIALRGMV    (#42, SEQ ID NO: 43)

MKKNDKIAAAIVLRGVA    (#43, SEQ ID NO: 44)

MKKNDQIVAAIALRGMV    (#51, SEQ ID NO: 45)

MKKNDKIAAAIALRGMG    (#52, SEQ ID NO: 46)

MKKNDQIGAAIALRGMV    (#53, SEQ ID NO: 47)

MKKNDQIGAAIALRGMG.   (#54, SEQ ID NO: 48)
```

The bolded residues represent differences from the peptide represented by SEQ ID NO:1.

Any of these peptides, or other peptides of the invention, can optionally contain a cysteine (C) residue at its N terminus, to facilitate the attachment of a biotin molecule, which can be useful for binding the peptide to a surface comprising avidin.

One aspect of the invention is a method for diagnosing Lyme disease in a subject (e.g. for diagnosing exposure to and/or infection by a pathogenic *Borrelia*), comprising measuring a bodily fluid (which would be expected to contain antibodies) of the subject for the presence of an antibody against a causative agent of Lyme disease (e.g. an antibody capable of binding to such an agent), wherein an elevated level of antibody in the subject compared to a corresponding level of antibody in a control (such as a known unaffected subject) indicates an infection by the causative agent and/or that the subject has Lyme disease. A "causative agent for Lyme disease," as used herein, includes a pathogenic species of *B. burgdorferi*, such as the three identified pathogenic species that are discussed above. Other species of *Borrelia* which have been implicated in Lyme disease, such as, e.g., *B. lusitaniae* and *B. valaisianae*, are also included, provided they induce antibodies which can react specifically with a peptide of the invention. It is to be understood that the term "pathogenic *Borrelia*," as used herein, refers to any such pathogenic genospecies that causes Lyme disease. "Lyme disease," as used herein, refers to an disease which exhibits the characteristics as summarized in Dattwyler, R. J. and Wormser, G. "Lyme borreliosis." in Infectious Diseases Medicine and Surgery (eds.) S. Gorbach and J. Bartlett, 3rd edition, Saunders Pub. New York, N.Y., 2003 and which is caused by a pathogenic *Borrelia*.

One embodiment of this method comprises contacting (incubating, reacting) a peptide of the invention with a sample of a biological fluid (e.g serum or CSF) from a subject (e.g. human or other animal) to be diagnosed (a subject suspected of having Lyme disease). In the presence of an antibody response to infection with a pathogenic *Borrelia*, an antigen-antibody complex is formed. The antigen-antibody complex is sometimes referred to herein as an antibody-peptide complex, a peptide-antibody complex, or an antibody-epitope complex; these terms are used interchangeably. Subsequently the reaction mixture is analyzed to determine the presence or absence of this antigen-antibody complex. A variety of conventional assay formats can be employed for the detection, such, e.g., as ELISA or lateral flow. The presence of an elevated amount of the antibody-peptide complex indicates that the subject was exposed to and infected with a pathogenic *Borrelia* capable of causing Lyme disease. In an ELISA assay, a positive response is defined as a value 2 or 3 standard deviations greater than the mean value of a group of healthy controls. In some embodiments, a second tier assay is required to provide an unequivocal sero-diagnosis of Lyme disease.

Peptides, compositions comprising the peptides (such as diagnostic compositions), kits and methods of the invention offer a number of advantages. For example, they allow for simple, inexpensive, rapid, sensitive and accurate detection of Lyme disease, and avoid serologic cross-reactivity with other conditions with "Lyme-like" symptoms, such as myalgias, arthralgias, malaise or fever, including conditions such as syphilis, chronic arthritis, and multiple sclerosis. This allows for an accurate diagnosis. Furthermore, a diagnostic test of the invention (e.g. an ELISA assay) is useful in serum samples that contain anti-OspA antibodies or other antibodies produced in response to a vaccine based on the outer surface proteins of *Borrelia*; a VlsE IR6 peptide of the invention does not cross-react with such antibodies, thereby allowing the differentiation of vaccinated individuals from individuals who were naturally infected with *B. burgdorferi*. In addition, the small size of a peptide of the invention allows it to be readily combined with other diagnostic peptides, e.g. from other *Borrelia* proteins, into a linear, multi-antigenic peptide for use in a diagnostic assay.

One aspect of the invention is an isolated peptide of the invention which binds specifically to an antibody induced by a causative agent of Lyme disease (a pathogenic *Borrelia*), e.g. in a sample from a subject having Lyme disease. An antibody "induced by" a pathogenic *Borrelia* is sometimes referred to herein as an antibody "against" the pathogenic *Borrelia*. An active variant my have one or more amino acid (e.g., conservative amino acid) replacements in, e.g., amino acids D4, I11, A12, Q6, A8, M16 and/or A17. Generally, a peptide of the invention is from the immunodominant invariable region 6 (IR6) of the VlsE protein of a pathogenic *Borrelia* species that causes Lyme disease.

Another aspect of the invention is a peptide of the invention that is associated with (e.g. coupled, fused or linked to, directly or indirectly) one or more additional moieties. The association may be, for example, via a terminal amino acid linker (such as Lys or Cys) or a chemical coupling agent. A peptide may be linked directly to one or more moieties, such as other peptides. For example, a peptide may be synthesized so as to contain a peptide of the invention flanked by one or more additional peptides (e.g. from *Borrelia*), on its N-terminus, its C-terminus, or both. In one embodiment, linked peptides are separated by a spacer. The spacer may consist, for example, of between about one and five (e.g., three) amino acids, preferably uncharged amino acids, e.g., aliphatic amino acids such as Gly or Ala. In one embodiment, the spacer is a triple Gly spacer. A linker may, e.g., provide distance between epitopes of different antigenic peptides. The additional moiety can be, e.g., a detectable label, a fusion partner (such as a chemical compound, or a peptide having an epitope from the same or a different protein from the same or a different pathogenic *Borrelia*), or a substrate that immobilizes the peptide (e.g. a microwell plate, an Immobilon or nitrocellulose membrane, or latex beads).

Another aspect of the invention is a diagnostic reagent, comprising a peptide of the invention and, optionally, a system for detecting a complex of the peptide and a specific antibody, and/or a substrate for immobilizing the peptide.

Another aspect of the invention is a composition comprising a peptide of the invention and, optionally, one or more additional polypeptides or peptides that specifically recognize antibodies to a causative agent of Lyme disease. The additional polypeptides or peptide(s) may be used in conjunction with a peptide of the invention as part of a cocktail; or one or more of the additional polypeptides or peptides may be fused at the N-terminus and/or the C-terminus of a peptide of the invention to form a fusion peptide or polypeptide. The terms peptide and polypeptide are used interchangeably herein; for example, an amino acid consisting of three 9-15-mer peptides linked directly to one another can be referred to as either a peptide or a polypeptide.

Another aspect of the invention is a kit for diagnosing Lyme disease in a subject, which comprises a peptide of the invention and optionally comprises one or more additional peptides or polypeptides as noted above. The peptide(s) may comprise a detectable label, or the kit may include a detection system (e.g. a labeled conjugate and a reagent) for detecting a peptide which is specifically bound to an antibody in the sample. In one embodiment, the kit contains a substrate for immobilizing the peptide, such as a microwell plate, an Immobilon or nitrocellulose membrane, or latex beads.

Another aspect of the invention is a method for diagnosing Lyme disease in a subject suspected of having antibodies against a causative agent of Lyme disease (e.g. for diagnosing exposure to and/or infection by a pathogenic *Borrelia*), comprising contacting a sample from the subject a with a peptide or composition of the invention, under conditions effective for the formation of a specific peptide/antibody complex, and detecting the presence (e.g. the amount) of a peptide/antibody complex. In one embodiment, the detection method is an enzyme-linked immunosorbent assay (ELISA); and/or is carried out in vitro.

An isolated peptide of the invention can be of any desirable size. For example, it can consist of, e.g., 17, 18, 19, 20, 21, 22, 23 or 24 amino acids. Representative such peptides include, e.g., the 18 amino acid peptide, MKKDDQIAAAIALRGMAK (SEQ ID NO:4), the 19 amino acid peptide, MKKDDQIAAAIALRGMAKD (SEQ ID NO:12), the 20 amino acid peptide, MKKDDQIAAAIALRGMAKDG (SEQ ID NO:13), the 21 amino acid peptide, MKKDDQIAAAIALRGMAKDGK (SEQ ID NO:14), the 22 amino acid peptide, MKKDDQIAAAIALRGMAKDGKF (SEQ ID NO:15), the 23 amino acid peptide, MKKDDQIAAAIALRGMAKDGKFA (SEQ ID NO:16), or the 24 amino acid peptide, MKKDDQLAAAIALRGMAKDGKFAV (SEQ ID NO:17). Other representative peptides include any of the other 17-mer or 18-mer peptides described herein, which further comprise, attached at the C-terminal end, one or more of the consecutive amino acids from the *B. burgdorferi* strain, KDGKFAV (SEQ ID NO:49), or one or more of the consecutive amino acids of from the *B. garinii* strain, KDGQFALKD (SEQ ID NO:50), or active variants of those sequences. Optionally, such a peptide can contain an N-terminal Cys or Lys residue, e.g. to facilitate the addition of a Biotin molecule. Furthermore, active variants of the peptides are included, e.g. in which one or more of D4, I11, A12, Q6, A8, M16 and/or A17 is substituted with an amino acid (e.g., a conservative amino acid) replacement. Such a peptide can be substituted for an isolated peptide consisting of the sequence of SEQ ID NO:1, in any of the compositions of matter or methods disclosed herein. For example, the peptide can be associated with a second moiety, used as a diagnostic reagent, present in a composition comprising one or more additional polypeptides or peptides that specifically recognize antibodies to a causative agent of Lyme disease, or present in a kit for diagnosing Lyme disease.

A peptide, including a modified form thereof, which "binds specifically" to ("is specific for"; binds "preferentially" to) an antibody against a pathogenic *Borrelia* interacts with the antibody, or forms or undergoes a physical association with it, in an amount and for a sufficient time to allow detection of the antibody. By "specifically" or "preferentially" is meant that the peptide has a higher affinity, e.g. a higher degree of selectivity, for such an antibody than for other antibodies in a sample. That is, the peptide has an affinity for the antibody of at least about 2-fold higher than for other antibodies in the sample. The affinity or degree of specificity can be determined by a variety of routine procedures, including, e.g., competitive binding studies.

An "isolated" peptide of the invention is in a form other than it occurs in nature, e.g. in a buffer, in a dry form awaiting reconstitution, as part of a kit, etc. In some embodiments, the peptide is substantially purified. The term "substantially purified", as used herein refers to a molecule, such as a peptide, that is substantially free of other proteins, lipids, carbohydrates, nucleic acids and other biological materials with which it is naturally associated. For example, a substantially pure molecule, such as a peptide, can be at least about 60%, by dry weight, preferably at least about 70%, 80%, 90%, 95%, or 99% the molecule of interest.

The invention includes a peptide represented by SEQ ID NO:1, as well as active variants of this peptide. An "active variant" of this peptide, or of other peptides described herein, refers to a peptide which retains the ability to specifically recognize (bind to) an antibody against a causative agent of Lyme disease.

An active variant peptide may contain, e.g., one or more (e.g., 1-4) amino acid additions, substitutions, deletions, insertions, inversions, fusions, and truncations or a combination of any of these. Substitutions may be of conservative or non-conservative amino acids. Conservative replacements are those that take place within a family of amino acids that are related in their side chains and chemical properties. These include, e.g., (1) acidic: aspartate, glutamate; (2) basic: lysine, arginine, histidine; (3) nonpolar: alanine, valine, leucine, isoleucine, proline, phenylalanine, methionine, tryptophan; (4) uncharged polar: glycine, asparagine, glutamine, cysteine, serine, threonine, tyrosine; (5) aliphatic: glycine, alanine, valine, leucine, isoleucine, serine, threonine, with serine and threonine optionally be grouped separately as aliphatic-hydroxyl; (6) aromatic: phenylalanine, tyrosine, tryptophan; (7) amide: asparagine, glutamine; and (9) sulfur-containing: cysteine and methionine (see, for example, Biochemistry, 2nd ed., Ed. by L. Stryer, W H Freeman and Co.: 1981). Whether a change in the amino acid sequence of a peptide results in an active variant can be readily determined by assessing the ability of the variant peptide to produce a response in e.g. an ELISA in a fashion similar to the wild-type peptide, or to competitively inhibit such a response. Peptides in which more than one replacement has been introduced can be readily tested in the same manner. Generally, between one and about four codon changes can be present in such a variant. In embodiments, one, two, three, or four such changes are present in a variant consisting of the 17 residue of SEQ ID NO:1. Muteins and analogs are included.

The identification of the peptide of SEQ ID NO:1 was obtained from the IR6 region of the *B. burgdorferi species, B. burgdorferi* sensu stricto. Active variants of this peptide include, e.g., peptides in which one or more of D4, I11 or A12 is substituted with an amino acid (e.g., a conservative amino acid) replacement. One example of such a variant is a peptide containing comparable residues from the IR6 region of *B. garinii*—MKKDDQIAAAMVLRGMA (SEQ ID NO:6), in which I11 is substituted with M, and A12 is substituted with V. Another suitable variant is the comparable 17 amino acid peptide from the IR6 region of the pathogenic variant, strain 297-MKKNDQIAAAIVLRGMA (SEQ ID NO:10)—in which D4 is substituted with N and A12 is substituted with V. See, e.g., the alignment of sequences in FIG. 2 of U.S. Pat. No. 6,475,492. A variety of combinations of altered amino acids at residues 4, 11 and 12 are thus encompassed by the invention, as are other naturally occurring variations in amino acid resides found in the IR6 region of other pathogenic *Borrelia.*

The inventors have also discovered that replacements of amino acid residues Q6, A8, M16 and/or A17 of SEQ ID NO:1 also fail to negatively impact the ability of a peptide to bind to an antibody generated following infection with a pathogenic *Borrelia*; thus, variant peptides having replacement amino acids (e.g., conserved amino acids) at one or more of these sites are also encompassed by the invention. Such variants are discussed further elsewhere in this application.

As is discussed in Example V, particular variants can be especially effective for diagnosing the presence of particular strains of pathogenic *Borrelia*. For example, a peptide consisting of SEQ ID NO:1 is particularly useful for detecting *B. burgdorferi* sensu stricto, e.g., in U.S. populations or in certain areas of Europe. A variant consisting of the sequence of SEQ ID NO:6 is particularly useful for detecting a strain of pathogenic *Borrelia* found in infected subjects in certain areas of Europe.

The peptides of the invention may be modified by a variety of techniques, such as by denaturation with heat and/or SDS. A peptide of the invention may be modified to provide an additional N- or C-terminal amino acid sequence suitable for biotinylation, e.g., cysteine or lysine; suitable for chemical lipidation, e.g., cysteine; or the like.

Peptides of the invention may be modified by any of a variety of known modifications. These include, but are not limited to, glycosylation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, ubiquitination, modifications with fatty acids, transfer-RNA mediated addition of amino acids to proteins such as arginylation, etc. Analogues of an amino acid (including unnatural amino acids) and peptides with substituted linkages are also included.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in many basic texts, such as Proteins—Structure and Molecular Properties, 2nd ed., T. E. Creighton, W.H. Freeman and Company, New York (1993). Many detailed reviews are available on this subject, such as by Wold, F., Posttranslationail Covalent Modification of Proteins, B. C. Johnson, Ed., Academic Press, New York 1-12 (1983); Seifter et al. (1990) Meth. Enzymol. 182:626-646 and Rattan et al. (1992) Ann. N.Y. Acad. Sci. 663:48-62.

Peptides of the invention that consist of any of the sequences discussed herein may be modified by any of the discussed modifications. Such peptides still "consist of" the amino acids.

Peptides of the invention may be associated with one or more further moieties. The association can be covalent or non-covalent, and can be, for example, via a terminal amino acid linker (such as Lys or Cys) or a chemical coupling agent. An additional moiety can be, e.g., a detectable label, a fusion partner (such as a chemical compound or a peptide having an epitope of another pathogenic *Borrelia*), or a substrate that immobilizes the peptide (e.g. a microwell plate, an Immobilon or nitrocellulose membrane, or latex beads).

A peptide of the invention can be fused to a fusion partner (e.g. a peptide or other moiety) that can be used to improve purification, to enhance expression of the peptide in a host cell, to aid in detection, to stabilize the peptide, etc. Examples of suitable compounds for fusion partners include polyethylene glycol, PEGylation, or other chemicals. Among the many suitable peptide or polypeptide fusion partners are, e.g., β-galactosidase, glutathione-S-transferase, a histidine tag, etc. In some embodiments, a peptide of the invention is provided with a detectable label, such as those described below.

A peptide of the invention can be associated with a substrate that immobilizes the peptide. The substrate can be, e.g., a solid or semi-solid carrier, support or surface. The association can be covalent or non-covalent, and can be facilitated by a moiety associated with the peptide that enables covalent or non-covalent binding, such as a moiety that has a high affinity to a component attached to the carrier, support or surface. For example, the peptide can be associated with a biotin moiety, and the component associated with the surface can be avidin. The peptide can be immobilized on the solid or semi-solid surface or carrier either prior to or after the addition of the sample containing antibody.

A peptide of the present invention can be in the form of a pharmaceutically acceptable salt. Suitable acids and bases that are capable of forming salts with the peptides of the present invention are well known to those of skill in the art, and include inorganic and organic acids and bases.

A peptide of the invention can be produced using conventional chemical synthesis techniques, such as those described, e.g., in G. Barony et al., The Peptides: Analysis, Synthesis & Biology, Academic Press, pp. 3-285 (1980). Such chemically synthesized peptides can be obtained from commercial suppliers. Peptides produced by chemical synthesis can be obtained at purities exceeding about 95%. Therefore, there is typically a much reduced likelihood for undesirable cross reactivity with random antibodies than by using peptides obtained by other methods.

Alternatively, a peptide of the invention can be produced recombinantly following conventional genetic engineering techniques. To produce a recombinant peptide of the invention, a nucleic acid encoding the peptide is inserted into a suitable expression system. Generally, a recombinant molecule or vector is constructed in which the polynucleotide sequence encoding the selected peptide is operably liked to an expression control sequence permitting expression of the peptide. Numerous types of appropriate expression vectors are known in the art, including, e.g., vectors containing bacterial, viral, yeast, fungal, insect or mammalian expression systems. Methods for obtaining and using such expression vectors are well-known. For guidance in this and other molecular biology techniques used for compositions or methods of the invention, see, e.g., Sambrook et al, Molecular Cloning, A Laboratory Manual, current edition, Cold Spring Harbor Laboratory, New York; Miller et al, Genetic Engineering, 8:277-298 (Plenum Press, current edition), Wu et al, *Methods in Gene Biotechnology* (CRC Press, New York, N.Y., current edition), *Recombinant Gene Expression Protocols*, in *Methods in Molecular Biology*, Vol. 62, (Tuan, ed., Humana Press, Totowa, N.J., current edition), and *Current Protocols in Molecular Biology*, (Ausabel et al, Eds.,) John Wiley & Sons, NY (current edition), and references cited therein.

Suitable host cells or cell lines for the recombinant nucleic acids or vectors of the invention transfection by this method include bacterial cells. For example, various strains of *E. coli* (e.g., HB101, MC1061) are well-known as host cells in the field of biotechnology. Various strains of *B. subtilis, Pseudomonas, Streptomyces*, and other bacilli and the like can also be employed in this method. Alternatively, a peptide of the invention can be expressed in yeast, insect, mammalian, or other cell types, using conventional procedures.

Thus, the present invention provides a method for producing a recombinant peptide or polypeptide, which involves transfecting or transforming, e.g., by conventional means such as electroporation, a host cell with at least one expression vector containing a polynucleotide of the invention under the control of an expression control sequence (e.g. a transcriptional regulatory sequence). The transfected or transformed host cell is then cultured under conditions that allow expression of the peptide or polypeptide. The expressed peptide or polypeptide is recovered, isolated, and optionally purified from the cell (or from the culture medium, if expressed extracellularly) by appropriate means known to one of skill in the art, including liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention. One skilled in the art can determine the purity of the peptide or polypeptide by using standard methods including, e.g., polyacrylamide gel electrophoresis (e.g. SDS-PAGE); column chromatography (e.g. high performance liquid chromatography (HPLC)), or amino-terminal amino acid analysis.

Included in the invention are a polynucleotide encoding and/or expressing a peptide or polypeptide of the invention, a vector comprising the polynucleotide, and a host cell comprising the polynucleotide acid or vector.

A peptide of the invention may be used in combination with one or more additional peptides or polypeptides from the same or a different protein, from the same or a different pathogenic *Borrelia* strain, wherein the additional peptide(s) or polypeptide(s) also bind specifically to an antibody against a pathogenic *Borrelia*. The combination may comprise a cocktail (a simple mixture) of individual peptides or polypeptide, or it may be in the form of a fusion peptide or polypeptide (a multimeric peptide). For example, a peptide of the invention may be fused at its N-terminus or C-terminus to another suitable peptide. Two or more copies of a peptide of the invention may be joined to one another, alone or in combination with one more additional peptides. Combinations of fused and unfused peptides or polypeptides can be used. In one embodiment, the additional peptide(s) contain B-cell and/or T-cell epitopes from a protein of a pathogenic *Borrelia*.

Suitable additional peptides or polypeptides (sometimes referred to herein as "antigenic peptides or polypeptides" or as "agents") can be derived from *Borrelia* antigens, such as OspA, OspB, DbpA, flagella-associated proteins FlaA(p37) and FlaB(p41), OspC (25 kd), BBK32, BmpA(p39), p21, p39, p66 or p83. See, e.g., Barbour et al (1984) *Infect. Immun.* 45, 94-100; Simpson et al. (1990) *J. Clin. Microbiol.* 28, 1329-1337; Hansen et al. (1988) *Infect. Immun.* 56, 2047-2053; Hansen et al. (1988) *Infect. J. Clin. Microbiol.* 26, 338-346; Wilske et al. (1986) *Zentral, Bakteriol, Parsitenkd, Infektionshkr, Hyg. Abt.* 1 Orig. Reihe, A. 263, 92-102; Dorward et al. (1991) *J. Clin. Microbiol.* 29, 1162-1170; published NTIS U.S. patent application No. 485,551; European patent application No. 465,204; International Patent Application No. PCT/US91/01500; International Patent Application No. PCT/EP90/02282; International Patent Application No. PCT/DK89/00248; International patent application No. WO92/00055. Polypeptides or peptides derived from other microorganisms can also be used.

One embodiment of the invention—a composition comprising a peptide of the invention and one or more additional agent(s)—is particularly well-suited for diagnosing *Borrelia* infections early after infection (e.g., within one to two weeks after the onset of infection). Among the pathogenic *Borrelia* proteins whose expression has been recognized in early human infection (e.g. to which IgM antibody appears early after infection) are OspC, BBK32, the flagella-associated protein, FlaB(p41), and, to a lesser extent, BmpA(p39), VlsE and the flagella-associated protein, FlaA(p37). Polypeptides or peptides which derive from those polypeptides are suitable for assays for early infection.

Some suitable linear epitopes which can be used for the diagnosis of early infection include peptides identified in OspC: PVVAESPKKP (SEQ ID NO:8), reported by Steere et al. (1987) *Ann. Intern Med.* 107, 725-731; ILMTLFLFIS-CNNS (SEQ ID NO:9), reported by AC Steere (2001) *N Engl J Med* 345, 115-25; and one or more epitopes contained between amino acids 161 and 210, reported by Jobe et al. (2003) *Clin Diagn Lab Immunol* 10, 573-8)]. The OspC peptides described in U.S. Pat. No. 6,716,574 can also be used. Other suitable regions, which have been shown not contain major cross-reactive epitopes, have been identified in FlaB (p41), e.g. residues 120 to 235. See, e.g., Crother et al. ((2003)

*Infect. Immun.* 71, 3419-3428 and Wang et al. (1999)) *Clin Microbial Rev* 12, 633-653. Other peptides bearing either linear or conformational epitopes are known in the art.

Variants of previously identified epitopes can be readily selected by one of skill in the art, based in part on known properties of the epitopes. For example, a known epitope may be lengthened or shortened, at one or both ends, by about 1-3 amino acids; one, two or more amino acids may be substituted by conservative amino acids; etc. Furthermore, if a region of a protein has been identified as containing a suitable epitope, an investigator can "shift" the region of interest (select different sub-sequences) up to about 5 amino acids in either direction from the endpoints of the original rough region, e.g. to optimize the activity. Methods for confirming that variant peptides are suitable are conventional and routine. Methods for identifying additional epitopes, particularly from variable regions rather than the conserved regions discussed above (e.g. from OspC, BBK32 or DbpA), are discussed in the Examples.

Polypeptides comprising linked peptides may be of any suitable length (e.g. between about 20-80 amino acids, or more), and they may contain any desirable number of linear epitopes (e.g. between about 2-5, or more). For example, between 3 to 5 peptides of about 9-15 amino acids each may be combined, optionally in the presence of suitable spacers, to generate a polypeptide of about 45-50 amino acids. A length of about 50 amino acids can be readily synthesized chemically by current technologies. Other methods may be used to generate longer peptides.

The peptides can be linked in any order. For example, an IR6 peptide of the invention may lie at the N-terminal end of a multipeptide, at the C-terminal end of a multipeptide, or between other peptides.

Example X illustrates and characterizes some representative multi-epitope peptides than can be used in methods and compositions of the invention. Each of these peptides comprises the 17 amino acid IR6 peptide represented by SEQ ID NO:1, linked either at its N-terminal or its C-terminal end to another *Borrelia* peptide. The other *Borrelia* peptides are Fla-13 (a 13 amino acid peptide from the p41 flagellin protein (VQEGVQQEGAQQP (SEQ ID NO:18)) and pepC-10 (a 10 amino acid peptide from the OspC protein (PVVAESPKKP (SEQ ID NO:8)). As shown in the Example, each of these multi-epitope peptides exhibits significantly more binding to sera from subjects infected with *Borrelia burgdorferi* sensu lato than does the 17 amino acid peptide represented by SEQ ID NO:1 or the 26 amino acid peptide derived from the same strain. A comparable 26 amino acid peptide derived from the European *Borrelia* species, *B. garinii*, represented by SEQ ID NO:2, is currently approved for use in diagnostic assays for Lyme Disease.

In one embodiment of the invention, a composition comprising a peptide of the invention as well as one of more of the above-mentioned additional peptides (e.g. in the form of a cocktail or a fusion peptide or polypeptide) is used in a single tier assay, for detecting early/or and late stage Lyme disease. Such a peptide cocktail or fusion polypeptide can be effective in the diagnosis of Lyme disease as caused by a wide spectrum of pathogenic *Borrelia* isolates.

Fusion peptides or polypeptides (multimeric proteins) of the invention can be produced recombinantly or synthesized chemically. They may also include a peptide of the invention fused or coupled to moieties other than amino acids, including lipids and carbohydrates.

One aspect of the invention is a method for detecting Lyme disease in a subject suspected of having antibody against a causative agent of Lyme disease. The diagnostic method is useful for diagnosing subjects exhibiting the clinical symptoms of, or suspected of having, Lyme disease.

The subject can be any subject (patient) in which antibodies can be made against the causative agent and detected. Typical subjects include vertebrates, such as mammals, including wildlife (e.g. mice and chipmunks), dogs, cats, non-human primates and humans.

In one embodiment, the diagnostic method involves detecting the presence of naturally occurring antibodies against pathogenic *Borrelia* (e.g. *B. Burgdorferi*) which are produced by the infected subject's immune system in its biological fluids or tissues, and which are capable of binding specifically to a peptide of the invention or combinations of a peptide of the invention and, optionally, one or more suitable additional antigenic polypeptides or peptides.

One embodiment of the invention is a diagnostic immunoassay method, which includes (1) taking a sample of body fluid or tissue likely to contain antibodies; (2) contacting the sample with a peptide of the invention, under conditions effective for the formation of a specific peptide-antibody complex (for specific binding of the peptide to the antibody), e.g., reacting or incubating the sample and a peptide; and (3) assaying the contacted (reacted) sample for the presence of an antibody-peptide reaction (e.g., determining the amount of an antibody-peptide complex).

As used herein, the singular forms "a,", "an," and "the" include plural referents unless the context clearly dictates otherwise. Thus, "a" peptide of the present invention, as used above, can be two or more peptides, which can be the same or different. Similarly, when an isolated peptide of the invention is in association with (e.g., linked to) "an" additional peptide, the isolated peptide can be associated with one or more additional peptides.

Phrases such as "sample containing an antibody" or "detecting an antibody in a sample" are not meant to exclude samples or determinations (detection attempts) where no antibody is contained or detected. In a general sense, this invention involves assays to determine whether an antibody produced in response to infection with a pathogenic *Borrelia* is present in a sample, irrespective of whether or not it is detected.

Conditions for reacting peptides and antibodies so that they react specifically are well-known to those of skill in the art. See, e.g., Current Protocols in Immunology (Coligan et al., editors, John Wiley & Sons, Inc) or the Examples herein.

The diagnostic method comprises taking a sample of body fluid or tissue likely to contain antibodies. The antibodies can be, e.g., of IgG, IgE, IgD, IgM, or IgA type. Generally, IgM and/or IgA antibodies are detected, e.g. for the detection of early infection. IgG antibodies can be detected when some of the additional peptides discussed above are used in the method (e.g. peptides for the detection of flagellum proteins). The sample is preferably easy to obtain and may be serum or plasma derived from a venous blood sample or even from a finger prick. Tissue from other body parts or other bodily fluids, such as cerebro-spinal fluid (CSF), saliva, gastric secretions, mucus, etc. are known to contain antibodies and may be used as a source of the sample.

Once the peptide antigen and sample antibody are permitted to react in a suitable medium, an assay is performed to determine the presence or absence of an antibody-peptide reaction. Among the many types of suitable assays, which will be evident to a skilled worker, are immunoprecipitation and agglutination assays.

In embodiments of the invention, the assay may comprise (1) immobilizing the antibody(s) in the sample, adding a peptide of the invention, and then detecting the degree of antibody bound to the peptide, e.g. by the peptide being labeled or by adding a labeled substance (conjugate, binding partner), such as a labeled antibody, which specifically recognizes the peptide; (2) immobilizing a peptide of the invention, adding the sample containing an antibody(s), and then detecting the amount of antibody bound to the peptide, e.g. by adding a labeled substance (conjugate, binding partner), such as a labeled antibody, which specifically recognizes the antibody; or (3) reacting the peptide and the sample containing antibody(s) without any of the reactants being immobilized, and then detecting the amount of complexes of antibody and peptide, e.g. by the peptide being labeled or by adding a labeled substance (conjugate, binding partner), such as a labeled antibody, which specifically recognizes the peptide.

Immobilization of a peptide of the invention can be either covalent or non-covalent, and the non-covalent immobilization can be non-specific (e.g. non-specific binding to a polystyrene surface in e.g. a microtiter well). Specific or semi-specific binding to a solid or semi-solid carrier, support or surface, can be achieved by the peptide having, associated with it, a moiety which enables its covalent or non-covalent binding to the solid or semi-solid carrier, support or surface. For example, the moiety can have affinity to a component attached to the carrier, support or surface. In this case, the moiety may be, e.g., a biotin or biotinyl group or an analogue thereof bound to an amino acid group of the peptide, such as 6-aminohexanoic acid, and the component is then avidin, streptavidin or an analogue thereof. An alternative is a situation in which the moiety has the amino acid sequence His-His-His-His-His-His (SEQ ID NO:11) and the carrier comprises a Nitrilotriacetic Acid derivative (NTA) charged with $Ni^{++}$ ions. Among suitable carriers, supports or surface are, e.g., magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles, red blood cells, mono- or polyclonal antibodies or Fab fragments of such antibodies.

The protocols for immunoassays using antigens for detection of specific antibodies are well known in art. For example, a conventional sandwich assay can be used, or a conventional competitive assay format can be used. For a discussion of some suitable types of assays, see Current Protocols in Immunology (supra). In a preferred assay, a peptide of the invention is immobilized to the solid or semi-solid surface or carrier by means of covalent or non-covalent binding, either prior to or after the addition of the sample containing antibody.

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices, dipsticks and immunocapillary or immunochromatographic immunoassay devices.

In embodiments of the invention, the solid or semi-solid surface or carrier is the floor or wall in a microtiter well; a filter surface or membrane (e.g. a nitrocellulose membrane or a PVDF (polyvinylidene fluoride) membrane, such as an Immobilon membrane); a hollow fiber; a beaded chromatographic medium (e.g. an agarose or polyacrylamide gel); a magnetic bead; a fibrous cellulose matrix; an HPLC matrix; an FPLC matrix; a substance having molecules of such a size that the molecules with the peptide bound thereto, when dissolved or dispersed in a liquid phase, can be retained by means of a filter; a substance capable of forming micelles or participating in the formation of micelles allowing a liquid phase to be changed or exchanged without entraining the micelles; a water-soluble polymer; or any other suitable carrier, support or surface.

In some embodiments of the invention, the peptide is provided with a suitable label which enables detection. Conventional labels may be used which are capable, alone or in concert with other compositions or compounds, of providing a detectable signal. Suitable detection methods include, e.g., detection of an agent which is tagged, directly or indirectly, with a fluorescent label by immunofluorescence microscopy, including confocal microscopy, or by flow cytometry (FACscan); detection of a radioactively labeled agent by autoradiography; electron microscopy; immunostaining; subcellular fractionation, or the like. In one embodiment, a radioactive element (e.g. a radioactive amino acid) is incorporated directly into a peptide chain; in another embodiment, a fluorescent label is associated with a peptide via biotin/avidin interaction, association with a fluorescein conjugated antibody, or the like. In one embodiment, a detectable specific binding partner for the antibody is added to the mixture. For example, the binding partner can be a detectable secondary antibody which binds to the first antibody. This secondary antibody can be labeled, e.g., with a radioactive, enzymatic, fluorescent, luminescent, or other detectable label, such as an avidin/biotin system.

A "detection system" for detecting bound peptide, as used herein, may comprise a detectable binding partner, such as an antibody specific for the peptide. In one embodiment, the binding partner is labeled directly. In another embodiment, the binding partner is attached to a signal generating reagent, such as an enzyme that, in the presence of a suitable substrate, can produce a detectable signal. A surface for immobilizing the peptide may optionally accompany the detection system.

In embodiments of the invention, the detection procedure comprises visibly inspecting the antibody-peptide complex for a color change, or inspecting the antibody-peptide complex for a physical-chemical change. Physical-chemical changes may occur with oxidation reactions or other chemical reactions. They may be detected by eye, using a spectrophotometer, or the like.

In one embodiment of the method, the peptide, or a mixture of peptides, is electro- or dot-blotted onto nitrocellulose paper. Subsequently, the biological fluid (e.g. serum or plasma) is incubated with the blotted antigen, and antibody in the biological fluid is allowed to bind to the antigen(s). The bound antibody can then be detected, e.g. by standard immunoenzymatic methods.

In another embodiment of the method, latex beads are conjugated to the antigen(s) of the invention. Subsequently, the biological fluid is incubated with the bead/peptide conjugate, thereby forming a reaction mixture. The reaction mixture is then analyzed to determine the presence of the antibodies.

One preferred assay for the screening of blood products or other physiological or biological fluids is an enzyme linked immunosorbant assay, i.e., an ELISA. Typically in an ELISA, the isolated antigen(s) of the invention is adsorbed to the surface of a microtiter well directly or through a capture matrix (i.e., antibody). Residual, non-specific protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing specific anti-pathogenic Borrelia (e.g. B. burgdoferi) antibody. The sample can be applied neat, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with an optimal concentration of an appropriate anti-immunoglobulin antibody (e.g., for human subjects, an anti-human immunoglobulin (αHuIg) from another animal, such as dog, mouse, cow, etc.) that is conjugated to an enzyme or other label by standard procedures and is dissolved in blocking buffer. The label can be chosen from a variety of enzymes, including horseradish peroxidase (HRP), β-galactosidase, alkaline phosphatase, glucose oxidase, etc. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length). The cutoff OD value may be defined as the mean OD+3 standard deviations (SDs) of at least 50 serum samples collected from individuals from an area where Lyme disease is not endemic, or by other such conventional definitions. In the case of a very specific assay, OD+2 SD can be used as a cutoff value.

In one embodiment of an ELISA, a peptide of the invention is immobilized on a surface, such as a ninety-six-well ELISA plate or equivalent solid phase that is coated with streptavidin or an equivalent biotin-binding compound at an optimal concentration in an alkaline coating buffer and incubated at 4° C. overnight. After a suitable number of washes with standard washing buffers, an optimal concentration of a biotinylated form of a composition/antigen of this invention dissolved in a conventional blocking buffer is applied to each well; a sample is added; and the assay proceeds as above.

See the Examples for typical conditions for performing ELISA assays.

Another useful assay format is a lateral flow format. Antibody to human or animal antibody or *staph* A or G protein antibodies is labeled with a signal generator or reporter (i.e. colloidal gold) that is dried and placed on a glass fiber pad (sample application pad). The diagnostic peptide is immobilized on membrane, such as a PVDF (polyvinylidene fluoride) membrane (e.g an Immobilon membrane (Millipore)) or a nitrocellulose membrane. When a solution of sample (blood, serum, etc) is applied to the sample application pad, it dissolves the colloidal gold labeled reporter and this binds to all antibodies in the sample. This mixture is transported into the next membrane (PVDF or nitrocellulose containing the diagnostic peptide) by capillary action. If antibodies against the diagnostic peptide are present, they bind to the diagnostic peptide striped on the membrane generating a signal. An additional antibody specific to the colloidal gold labeled antibody (such as goat anti-mouse IgG) is used to produce a control signal.

It should be understood by one of skill in the art that any number of conventional protein assay formats, particularly immunoassay formats, may be designed to utilize the isolated peptides of this invention for the detection of pathogenic Borelia (e.g. B. burgdorferi) infection a subject. This invention is thus not limited by the selection of the particular assay format, and is believed to encompass assay formats that are known to those of skill in the art.

Reagents for ELISA or other assays according to this invention can be provided in the form of kits. Such kits are useful for diagnosing infection with a pathogenic Borrelia (e.g. a B. burgdorferi), using a sample from a subject (e.g. a human or other animal). Such a diagnostic kit can contain an peptide of the invention (and, if desired, additional peptides as discussed above) and, optionally, a system for (means enabling) detection of a peptide of the invention bound to an antibody against a protein from a pathogenic Borrelia, and/or a surface to which the peptide can be bound. In one embodiment, a kit contains a mixture of suitable peptides or means for preparing such mixtures, and/or reagents for detecting peptide-antibody complexes.

The kit can include microtiter plates to which the peptide(s) of the invention have been pre-adsorbed, another appropriate assay device, various diluents and buffers, labeled conjugates or other agents for the detection of specifically bound antigens or antibodies, and other signal-generating reagents, such as enzyme substrates, cofactors and chromogens. Other components of a kit can easily be determined by one of skill in the art. Such components may include coating reagents, polyclonal or monoclonal capture antibodies specific for a peptide of the invention, or a cocktail of two or more of the antibodies, purified or semi-purified extracts of these antigens as standards, MAb detector antibodies, an anti-mouse or anti-human antibody with indicator molecule conjugated thereto, an ELISA plate prepared for absorption, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptide-antibody complex. Such kits provide a convenient, efficient way for a clinical laboratory to diagnose infection by a pathogenic Borrelia, such as a B. burgdorferi.

Another aspect of the invention is an isolated antibody, antigen-specific antibody fragment, or other specific binding partner, which is specific for a peptide of the invention, e.g., wherein said antibody, antigen-specific antibody fragment, or specific binding partner is specific for the peptide of SEQ ID NO:1, SEQ ID NO:39, or one of the other peptides of the invention. Antibodies, e.g. polyclonal, monoclonal, recombinant, chimeric, humanized, single-chain, Fab, and fragments thereof, can be prepared according to any desired method. See also screening recombinant immunoglobulin libraries (e.g., Orlandi et al. (1989) *Proc. Natl. Acad. Sci. USA* 86, 3833-3837; Huse et al. (1989) *Science* 256, 1275-1281); and in vitro stimulation of lymphocyte populations (Winter et al. (1991) *Nature* 349, 293-299). The antibodies can be IgM, IgG, subtypes, IgG2a, IgG1, etc. Antibodies can be used from any source, including, goat, rabbit, mouse, chicken, etc. An antibody specific for a peptide means that the antibody recognizes a defined sequence of amino acids within or including the peptide. Other specific binding partners include, e.g., aptamers and PNA. The preparation of polyclonal antibodies is well-known to those skilled in the art. See, for example, Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992). The preparation of monoclonal antibodies likewise is conventional. See, for example, Kohler & Milstein (1975) *Nature* 256, 495; Coligan et al., sections 2.5.1-2.6.7; and Harlow et al., Antibodies: A Laboratory Manual, page 726 (Cold Spring Harbor Pub. 1988).

An isolated antibody, antigen-specific antibody fragment, or other specific binding partner of the invention can be used for a variety of applications, including therapeutic and diagnostic applications. By an "isolated" antibody is meant herein an antibody molecule that is removed from its original environment (e.g., the natural environment if it is naturally occurring), and is isolated or separated from at least one other component with which it is naturally associated. For example, a naturally-occurring antibody present in its natural living host is not isolated, but the same antibody, separated from some or all of the coexisting materials in the natural system, is isolated. Such antibodies could be part of a composition, and still be isolated in that such composition is not part of its natural environment One aspect of the invention is a method for detecting in a subject the presence of a naturally occurring IR6 antigen, itself, in its association with a pathogenic *Borrelia*, using an isolated antibody of the invention. The method can be used to determine that a subject has been exposed to, or infected by, a pathogenic *Borrelia*. In one embodiment, the method comprises contacting a sample (e.g. a bodily fluid or tissue suspected of containing a pathogenic *Borrelia*) from a subject with an antibody of the invention, under conditions effective for the formation of a specific antigen-antibody reaction. Preferably, the antibody is conventionally labeled, either directly or indirectly, for detection, e.g., with an enzyme such as HRP, avidin or biotin, chemiluminescent reagents, etc. Following the binding of the antibody to the antigen, excess labeled antibody is optionally removed, and the reaction mixture is analyzed to determine the presence or absence of the antigen-antibody complex and the amount of label associated therewith.

In one embodiment, a monoclonal or polyclonal antibody of the invention (which is capable of binding to the antigen) is bound to an ELISA plate. A sample, such as a biological fluid, is incubated on the antibody-bound plate and washed. Detection of an antigen-antibody complex and qualitative measurement of the labeled antibody are performed conventionally.

Other useful assay formats include the filter cup and dipstick. In the former assay, an antibody of the invention is fixed to a sintered glass filter to the opening of a small cap. The biological fluid or sample (e.g., about 5 mL) is worked through the filter. If the antigen is present (e.g. following infection with a pathogenic *Borrelia*), it will bind to the filter which can then be visualized through a second antibody/detector. The dipstick assay involves fixing an antigen or antibody to a filter, which is then dipped in the biological fluid, dried and screened with a detector molecule.

Kits for conducting this or other assay methods, using an antibody, antigen-specific antibody fragment, or other specific binding partner of the invention, are also included in the invention.

Much of the preceding discussion is directed to the detection of antibodies against pathogenic *Borrelia*. However, it is to be understood that the discussion also applies to the detection of primed T-cells, either in vitro or in vivo.

It is expected that a cell-mediated immune response (e.g. a T-helper response) is generated, since IgG is produced. It is therefore expected that it will be possible to determine the immunological reactivity between primed T-cells and a peptide of the invention. In vitro this can be done by incubating T-cells isolated from the subject with a peptide of the invention and measuring the immunoreactivity, e.g. by measuring subsequent T-cell proliferation or by measuring release of cytokines from the T-cells, such as IFN-.gamma; these methods are well-known in the art.

When a method of the invention is carried out in vivo, any of a variety of conventional assays can be used. For example, one can perform an assay in the form of a skin test, i.e. by intradermally injecting, in the subject, a peptide of the invention A positive skin reaction at the location of injection indicates that the subject has been exposed to and infected with a pathogenic *Borrelia* capable of causing Lyme disease, and a negative skin response at the location of injection indicates that the subject has not been so exposed/infected. This or other in vivo tests rely on the detection of a T-cell response in the subject.

In the foregoing and in the following examples, all temperatures are set forth in uncorrected degrees Celsius; and, unless otherwise indicated, all parts and percentages are by weight.

EXAMPLES

Example I

Material and Methods

The following methods were used for the experiments in Examples II-VI and X-XI and will be used for the experiments in Examples VII-IX.

A. Peptide Synthesis:

Synthetic peptides are custom synthesized by the Keck Biopolymer Resource at Yale University, by automated solid phase methodology using FMOC N-protection protocols.

B. ELISA Procedure

Solutions of purified peptides (and control proteins) in 100 mM BIS-TRIS propane buffer (pH9.7) are used to coat commercial microwell plates (MAXISORP™, Nunc (a polystyrene based modified surface)) at 5 μg/ml. The coating procedure is as follows: 100 μl of a solution containing the appropriate concentration of antigen is added to each well and the microwell plate incubated either for 1 h at room temperature or overnight at 4° C. The antigen solution is removed from the wells; the plate washed three times with phosphate buffered saline, pH 9 (PBS); and 300 μl of a conventional blocking solution (e.g., 100 mM BIS-TRIS propane buffer pH9.7, 0.10% Tween 20, 3% skim milk) added. Following a 30-minute incubation at 37° C., the plates are washed three times with TBST buffer, wrapped in plastic and stored at 4° C. until used. The standard blocking protocol successfully saturates this high antigen binding capacity, leaving low background readings in the control channels. A protein concentration of about 5 μg/ml in the coating buffer is optimal. Although the amount of each peptide bound to the surface and the amount of any one epitope exposed to the solution varies somewhat, the amount of bound epitope is not limiting within the useful range of the ELISA.

A standard procedure for the ELISA tests is employed. For example, human sera is diluted at 1:50 in 100 ul of TBST buffer with 1% skim milk. The samples are added in each well and the plate is incubated for 1 h at room temperature. Plates are washed three times with TBST buffer. The alkaline phosphates conjugated anti-human IgG (H+L) (Jackson ImmunoResearch, West Grove, Pa.) antibody is diluted at 1:1,600 in TBST buffer with 1% skim milk; 100 ul of this solution is dispensed onto the plate and incubated for 30 minutes at room temperature. Plates are washed three times with TBST buffer and 100 ul of substrate is added (pNPP Microwell Substrate System, KPL, Gaithersburg, Md.) and incubated for 1 h at room temperature. Plates are read at 405 nm on a microplate reader (Molecular Devices, Spectramax 320). A sample is considered positive if it produced an average absorbance superior to the mean of five negative controls plus three standard deviations. As an alternative, HRP (horseradish peroxidase) can be used as a secondary antibody. In this case, a PBS based buffer is generally used throughout the assay.

C. Immobilization of Biotinylpeptide-Streptavidin Conjugates in an ELISA Format.

Biotinylpeptide-Strepavidin conjugates in sodium phosphate buffer are used to coat microwell plates (MAXISORP™, Nunc (a polystyrene based modified surface)). The coating procedure is as follows: antigen is added to each well and the microwell plate incubated either for 1 h at room temperature or overnight at 4 C. The antigen solution is removed from the wells, the plate washed three times with PBS, and 200ul of blocking solution (2% bovine serum albumin fraction V (Sigma) in PBS added. Following a 30 min incubation at 37 C, the plates are washed three times with PBS, wrapped in plastic and stored at 4° C. until used. The binding of the peptides is monitored by ELISA using monoclonal antibodies specific for a control chimeric protein that are coated as Biotinylprotein-Strepavidin. A protein concentration of about 5 ug/ml in the coating buffer is optimal.

D. Test Panels.

We have access to a large bank of sera from well characterized culture confirmed patients (over 250 from patients at presentation with local EM) and from patients with late disease who had the presence of DNA from *B. burgdorferi* in clinical samples confirmed by PCR. Our test panels use sera selected from our bank and include sera from patients with early and late Lyme disease. Sera from patients with syphilis, and with rheumatologic disorders (rheumatoid arthritis and systemic lupus erythematosus) and other infectious diseases, as well as from normal healthy donors, are utilized as controls. The Lyme serum panels are representative of the population of suburban New York and include samples from children, adults, males, females, whites and minorities. In addition we have access to a large panel of serum from patients who were vaccinated with recombinant Osp A as part of vaccine efficacy trials. Sera from normal healthy individuals with neither a known history of Lyme disease nor immunoblot patterns characteristic of the infection obtained from areas endemic and non-endemic for LD are used as negative healthy controls.

E. Statistical Analysis.

The Odds Ratio (OR) method is used to assess statistical significance. The odds ratio is a measure of effect size particularly important in logistic regression that is a statistical regression model for Bernoulli-distributed dependent variables. OR is defined as the ratio of the odds of an event occurring in one group to the odds of it occurring in another group.

Example II

Comparison of 26-mer Immunodominant Peptides from a Conserved Region of VlsE from Two Pathogenic Genospecies, *B. Garinii* and *B. Burgdorferi* Senso Stricto (Strain B31)

An approved first tier assay for the serodiagnosis of Lyme disease, referred to as the "C6 peptide assay," is based on a conserved region of VlsE. The variable surface antigen of *B. burgdorferi* VlsE contains a 26 amino acid immunodominant region, IR6, that was reported to map as a single antigenic determinant in humans (see, e.g., Liang et al. (1999b) *Infect. Immun.* 67, 6702-06); U.S. Pat. No. 6,475,49; and Liang et al. (2000), supra). The sequence used to design the C6 peptide (PT7) was from a *B. garinii* strain, a strain not found in North America. A comparison of the amino acid differences between the IR6 sequences from *B. garinii* (PT7, strain IP90) and *B. burgdorferi* senso stricto (strain B31), a prototypic North American strain, is shown in Table 1. We synthesized the IR6 segments from both strains with N-terminal cysteinyl residues appended for attachment of biotinyl ligands as described by Liang et al. (1999c) *J Immunol* 163, 5566-73 and Liang et al. (1999a) *J Clin Microbiol* 37, 3990-6, and compared the two against a panel of 52 acute Lyme disease sera (erythema migrans, culture positive defined), 33 of which were culture confirmed. This panel was randomly selected from our serum bank (from the SUNY Stony Brook Lyme disease Center). They were not pre-selected in any way. The results of the IR6 assay on two different genus of *Borrelia* are shown in Table 1 below:

TABLE 1

Comparison between *B. garinii* (Bg) and *B. burgdorferi* (Bb) IR6 test sensitivity

| Peptides | Sequence | N. Pos./Total (%) | OR |
|---|---|---|---|
| BgIP90-26 | CMKKDDQIAAAMVLRGMAKDGQFALK | 23/55 (41.8%) | 1.787 |
| BbB31-26 | CMKKDDQIAAA I ALRGMAKDGKFAVK | 31/55 (56.4%) | |

The 25-residue segments correspond to the IR6 immunodominant regions of VlsE in the respective *B. burgdorferi* sensu lato strains, IP90 is *B. garinii* and B31 is *B. burgdorferi* sensu stricto. An N-terminal C (cysteine) was appended, e.g. for purposes of biothinylation. The BgIP90-26 peptide is represented by SEQ ID NO: 2. The BpB31-26 peptide is represented by SEQ ID NO: 3. Bold residues in the *B. burgdorferi* B31 sequence differ from the *B. garinii* IP90 sequence. Lyme diseasse panel used: 55 acute characterized by erythema migrans (EM) in the first month of infection; OR, Odds Ratio.

We observed that the peptide that was based on the *B. garinii* sequence (IP90-26) was less sensitive (41.8%) than the peptide based on the *B. burgdorferi* B31 sequence (B31-26, 56.4%). An Odds Ratio (OR) of 1.787 indicates the *B. burgdorferi* sequence is ~1.8 times as likely to be more sensitive than the *B. garinii* sequence.

Example III

Defining a Minimal Epitope in the IR6 Region

In order to determine the minimum human active epitope(s) in this region and to maximize the coverage of the natural variation for diagnostic purposes, we employed a finely detailed mapping strategy, working from the natural sequence matrix, and used a human sera panel obtained from patients with culture confirmed acute Lyme disease presenting with erythema migrans. We shortened the 26-residue sequence of IR6 from the C-terminus until its efficiency in detecting Early Lyme disease antibodies dropped sharply after the deletion of the C-terminal eight residues. We then returned to the sequence of IR6 shortened by seven residues at the C-terminus and began deleting residues from the N-terminus. The results are shown in Table 2. Two of the peptides in Table 2 have, at their N-terminal ends, a C residue, which was appended, e.g., to facilitate biotinylation of the peptide.

We unexpectedly found that shortening the C terminal portion of the peptide by 7 and 8 amino acids showed a trend toward increased its sensitivity (B31-18 vs B31-26, OR=1.552) which indicates that B31-18 is 1.5 times as likely to be more sensitive than B31-26 against the panel tested. By contrast, deletion of the $9^{th}$ C terminal residue (B31-16Ct) and deletion of the first N-terminal residue (B31-16Nt) caused a decline in the B31-18 peptide antibody detection. Odds Ratio between IR6-18 and IR6-16Ct is 2.009, which indicates that IR6-18 is twice as likely to be more sensitive than IR6-1 Ct. Thus, the critical immunodiagnostic epitope of the 26-residue IR6 sequence is confined within a 17-residue segment of the IR6 sequence and the N-terminal sequence (Met) is essential for maintenance of antigenicity. We refer to this more narrowly defined segment as B31-IR6-17 or, if an added N-terminal C residue is present, e.g. for the purposes of biotinylation, as B-31-IR6-18.

TABLE 2

Minimal Immunodominant Region in VlsE IR6 in *B. burgdorferi* B31

| Peptides | Sequence | | % Positive | OR |
|---|---|---|---|---|
| IR6-26 | CMKKDDQIAAAIALRGMAKDGKFAVK | (SEQ ID NO: 3) | 33%α | α1.552 |
| B31-IR6-18 | MKKDDQIAAAIALRGMAK | (SEQ ID NO: 4) | 36% | |
| B31-IR6-18 | CMKKDDQIAAAIALRGMA | (SEQ ID NO: 19) | 39% | |
| B31-IR6-16Ct | MKKDDQIAAAIALRGM | (SEQ ID NO: 5) | 24%β | β2.009 |
| B31-IR6-16Nt | KKDDQIAAAIALRGMA | (SEQ ID NO: 7) | 33% | |

The peptides correspond to the IR6 immunodominant regions of VlsE in *B. burgdorferi* sensu stricto. An N-terminal C (cysteine) was appended to two of the peptides, e.g. for purposes of biotinylation. Percentages shown correspond to positive results against a panel of 33 Acute Lyme disease sera (erythema migrans, culture positive defined) on ELISA. OR, Odds Ratio. Note that efficiency in detection of *B. burgdorferi* antibodies drops sharply (but not completely) with removal of residues from either end of the 17-mer core sequence MKKDDQIAAAIALRGMA (SEQ ID NO:1).

Example IV

Sensitivity and Specificity

We compared this narrowly defined peptide from *B. burgdorferi* (B31-17) to the homologous sequence from *B. garinii* (IP90-17) as well as to the respective 25-residue peptides, B31-25 and IP90-25. All of these tested peptides contained an added N-terminal cysteine, so they are referred to in the Tables below as B31-18, IP90-18, B31-26 and IP90-26. Sensitivity and specificity (Tables 3-5) of the four peptides was determined using several panels of clinically defined Lyme disease sera.

TABLE 3

Comparison between the four IR6 peptides for sensitivity

| | | N. of Positives (%) | | | |
|---|---|---|---|---|---|
| | n | B31-26 | IP90-26 | B31-18 | IP90-18 |
| Acute, Single EM OR | 42 | 19 (45.2%)αβ | 15 (35.7%)α α1.479 | 16 (38.0%)β β1.292 | 15 (35.7%) |
| Acute Dsm, Multiple EM | 5 | 3 (60.0%) | 3 (60.0%) | 3 (60.0%) | 3 (60.0%) |
| Acute, Neurologic | 6 | 5 (83.3%) | 5 (83.3%) | 5 (83.3%) | 5 (83.3%) |
| Late Lyme OR | 15 | 9 (60.0%)Φ Φ.683 | 7 (46.7%)Φ | 9 (60.0%) | 9 (60.0%) |
| Lyme re-infected | 5 | 5 (100%) | 5 (100%) | 5 (100%) | 5 (100%) |
| TOTAL | 73 | 41 (56%) | 35 (48%) | 38 (52%) | 37 (51%) |

Acute Dsm, Acute disseminated; EM, erythema migrans; OR, Odds Ratio.

Differences in sensitivity between the four peptides were significant in detecting *B. burgdorferi* antibodies in the panel defined as acute, single erythema migrans, early Lyme disease (Table 3 and Table 5). The peptide B31-26 is ~1.5 times as likely to be more sensitive than IP90-26mer and -18, and ~1.3 times as likely to be more sensitive than B31-18 against this panel. In the panel defined as Late Lyme, we observed that the B31-26 is 1.6 times as likely to be more sensitive than the IP90-26 and no differences were observed between B31-26 and the B31 and IP90-18mer peptides. Overall, we conclude that the peptide based on the *B. burgdorferi* sensu stricto sequence (B31) is more sensitive than the *B. garinii* (EP90), the sequence used to develop the C6 assay. There was no difference in sensitivity between the four peptides in detecting antibodies in sera from patients with specific symptoms of Lyme disease, such as the sera defined in three other panels, acute disseminated (60%), acute neurologic (83.3%), and Lyme re-infected (100%).

TABLE 4

Comparison between the four peptides for specificity

|  | n | B31-26 | IP90-26 | B31-18 | IP90-18 |
|---|---|---|---|---|---|
| RA | 34 | 0 (0%) | 2 (5.8%) | 1 (2.9%) | 3 (8.8%) |
| Syphilis | 27 | 2 (7.4%) | 1 (3.7%) | 1 (3.7%) | 3 (11.1%) |
| SLE | 20 | 1 (5%) | 0 (0%) | 1 (5%) | 3 (15%) |
| Healthy | 50 | 2 (4%) | 3 (6%) | 3 (6%) | 4 (8%) |
| Total | 131 | 5 (3.8%)α | 6 (4.6%) | 6 (4.6%)β | 13 (9.9%)αβ |
| OR |  | α2.766 |  | β2.288 |  |

RA, rheymatoid arthritis; SLE, systemic lupus erythematosus; OR, Odds Ratio.

TABLE 5

Comparison of the sensitivity and specificity of the four IR6 peptides

|  | n | B31-26 | IP90-26 | B31-18 | IP90-18 |
|---|---|---|---|---|---|
| Sensitivity | 73 | 56% | 48% | 52% | 51% |
| Specificity | 131 | 96.2% | 95.4% | 95.4% | 90.1% |

We tested the specificity of the assay against sera from patients with conditions whose clinical presentation could place Lyme disease in their differential diagnosis (rheumatoid arthritis) or that produce antibodies that can be potentially cross-reactive with anti-*B. burgdorferi* antibodies (syphilis and systhemic lupus erythematosus). Sera from healthy individuals from an endemic area was used as a negative control. The most specific peptides were B31-26, IP90-26 and B31-18 that detected the lowest number of cross-reactive samples (Table 4 and Table 5). The IP90-18 residue peptide was less specific than the other three peptides, detecting the highest percentages of cross-reactive antibodies. This peptide was 2.7 times as likely to detect cross-reactive antibodies than B31-26 and 2.3 times as likely to detect cross-reactive antibodies than B31-18 and IP90-26. The lack of specificity of this peptide against all cross-reactivity panels indicates that it is not appropriate for development of an assay to be used in the US.

In summary (Table 5), we conclude that the IR6 peptides based on the *B. burgdorferi* sensu stricto sequence (B31) showed the highest sensitivity and specificity to detect Lyme disease antibodies and that odds ratio (OR) determinations between the B31-26 and -18 residue peptides is equivalent (B31-18 vs -26, OR=~1.5, against one panel of early LD; and B31-26 vs -18, OR=~1.3 against a second panel of early LD).

Example V

Sensitivity to Lyme Disease Panels Obtained from Europe

We compared the sensitivity of the four peptides to two Lyme disease panels obtained from Europe, a panel from clinically defined Lyme disease Austrian patients and a second panel comprising sera from patients with signs and symptoms suggestive of Lyme disease from Portuguese patients (Table 6). We found that the B31-26 peptide was ~1.3 times as likely to be more sensitive to detect *B. burgdorferi* sensu lato antibodies from patients in the Austrian panel as compared to the IP90-26, and that the IP90-26 peptide was ~2.5 times as likely to be more sensitive in detecting anti-*B. burgdorferi* sensu lato antibodies from patients in the Portuguese panel as compared to B31-26. These findings contradict a previously published conclusion that the IR6 (C6) peptide from IP90 is able to interact significantly with antisera generated against subjects infected with *Borrelia* species other than *B. Garinii*, the species from which the IR6 peptide sequence was generated.

TABLE 6

Comparison between the four IR6 peptides using European sera panels

|  | n | B31-26 | IP90-26 | B31-18 | IP90-18 |
|---|---|---|---|---|---|
| Austrian | 30 | 11 (37%)α | 9 (30%)α | 10 (33%) | 8 (27%) |
| OR |  | α1.291 |  |  |  |
| Portuguese | 100 | 17 (17%)β | 22 (22%)β | 8 (8%) | 13 (13%) |
| OR |  |  | β2.492 |  |  |

OR, Odds Ratio

Example VI

Characterization of OspC

A. Infection at Secondary Sites is Limited to Four ospC Groups

OspC is an essential virulence factor that must be expressed by *B. burgdorferi* in the skin of the host mammal for infection to occur. We compared the ospC alleles in 162 human isolates of *B. burgdorferi* and found that infection at secondary sites was limited to just four ospC groups (A, B, I and K) (31) (Table 7 below). This table includes the data from GenBank, analysis of strains from CDC, strains from ticks collected from Shelter Island, N.Y., and strains isolated from patients seen at the SUNY at Stony Brook, Lyme Disease Center. The human isolates are heterogeneous in their geographic distribution. However, much of the tick data comes from eastern Long Island but has a pattern that looks the same as that found in other areas. Analysis of ospC genotype in human disease suggests that a restricted number of genotypes cause invasive disease (A, B, I and K). Other strains, such as C and N, cause EM but do not spread to secondary sites.

B. Different ospC Groups Seem to Represent Serotypes

We prospectively analyzed *B. burgdorferi* isolated from patients with Lyme disease by Single Strand Conformation Polymorphism (SSCP) to determine the ospC groups. *Borrelia* was isolated from primary erythema migrans lesions, blood or cerebrospinal fluid of patients seen at the Lyme Disease Center at SUNY, Stony Brook, N.Y. DNA was isolated from the bacteria and the ospC gene was amplified by semi-nested PCR with primers designed to bind in the conserved flanking regions of the gene. This PCR product was then run side by side on a 20% TBE gel at 8° C. for 17 h at 240V to reveal discernable mobility shifts between them. This SSCP analysis relies on the fact that the electrophoretic mobility of a nucleic acid in a non-denaturing gel is sensitive to both its length and shape. Different ospC types run at different molecular weights. These patterns are typed as C1, C2 etc, when run side by side against a known control. The PCR amplified DNA was also sequenced to confirm the ospC type. The serum correspondent to the typed genomic sample (from the same patient) was then labeled with the analogous ospC type. Of the 21 major groups of ospC classified, we used the sera typed as C1 (group A), C2 (group B), C10 (group I) and C12 (group K) since these were found at secondary sites of infection. On Western Blot and ELISA, we found that, in general, SSCP OspC typed serum reacted best with the corresponding recombinant OspC protein. For example, C1 serum reacted with C1 and C10 recombinant proteins; C2 serum reacted with C2 and C1 proteins; C10 serum reacted with C10 protein; C12 serum reacted with C12 and C1 proteins. Although OspC has epitopes that are common to all OspC's, our data indicate that these different ospC genotypes could represent serotypes. On the basis of these studies, we will focus on OspC1, C2, C10 and C12 to perform epitope mapping to identify divergent epitopes in order to improve coverage of genetic variations in pathogenic *B. burgdorferi*. We will initially our efforts on the most common, C1 and C12.

TABLE 7

| Major ospC Group | Ticks | Human Skin | CSF/BL/SF* |
|---|---|---|---|
| A | 17 | 23 | 21 |
| B | 17 | 19 | 4 |
| C | 11 | 3 | |
| D | 10 | 1 | |
| E | 6 | 1 | |
| F | 9 | | |
| G | 5 | 7 | |
| H | 7 | 6 | |
| I | 1 | 9 | 3 |
| J | 3 | 7 | |
| K | 6 | 32 | 16 |
| L | 2 | | |
| M | 1 | 3 | |
| N | 1 | 3 | |
| O | 1 | 1 | |

TABLE 7-continued

| Major ospC Group | Ticks | Human Skin | CSF/BL/SF* |
|---|---|---|---|
| T | | 1 | |
| U | | 2 | |

*Human isolates from CSF (cerebrospinal fluid), BL (blood) and SF (synovial fluid).

Example VII

Mapping Linear Epitopes of Additional *Borrelia Burgdorferi* Proteins

In order to design peptide based immunoassays with increased sensitivity in early disease, we will map the linear epitopes of several genes which elicit immune responses early in infection, including BBK32, DbpA and two OspC genotypes, OspC1 (OC group A), and C12 (OC group K).

It has previously been shown that, when the frequency of ospC clonal groups collected from infected ticks is compared to those from *B. burgdorferi* cultured from either human skin or invasive human infections, it becomes clear that only a small subset of the ospC clonal groups are associated with invasive human disease (i.e. are pathogenic). In developing peptide antigens to give maximum coverage of genetic diversity within the subset of pathogenic *B. burgdorferi*, we have chosen ospC sequences from the two most common of these four ospC invasive pathogenic clonal groups, OspC1 and C12. Recombinant purified OspC1 and OspC12 proteins are available in our laboratory. We will clone and purify BBK32 and DpbA for this project. DbpA has been used successfully to increase sensitivity of diagnostic assays for late stage Lyme disease in Europe. Because this antigen is also a good diagnostic candidate, we will also perform epitope mapping of DbpA. These will be tested individually against LD sera to determine antigen efficacy for detection of early LD. Continuous B-cell epitopes of the four proteins will be analyzed utilizing the Multipin Peptide Technology (PepScan).

A. Epitope mapping of OspC.

On the basis of our sequencing analysis of the various OspC's, we can predict both the conserved and the hypervariable regions containing epitopes for each genotype. Analysis of continuous B-cell epitopes will be carried out by means of the Multipin Peptide Technology (PepScan) of Chiron Mimotopes (San Diego, Calif.). The amino acid sequence of each portion of interest will be used to synthesize a complete set of overlapping dodecapeptides. These will be covalently attached to the surfaces of derivatized polyethylene pins in a format compatible with standard enzyme-linked immunosorbent assays (ELISAs). These overlapping peptides will cover the regions of interest. We will begin by analyzing the sequence 161 to 210 because it is known to contain several important epitopes. If we don't find immunogenic peptides in this area, we will map the entire sequence of OspC1. In addition, because there are identical regions between OspC1 and OspC12, we will focus on the divergent sequences of OspC12. The epitopes of BBK32 and DbpA have not been defined. We will map the entire *B. burgdorferi* B31 BBK32 and DbpA proteins.

The reactivities of various anti-OspC antibodies (from both sera from patients with Lyme disease and mouse monoclonal antibodies raised against OspC) with the pin-bound peptides will be detected by a modified enzyme immunoassay. Briefly, pins are precoated for 1 h at room temperature with 200 µl of PBS containing 3% bovine serum albumin (BSA) per well in the wells of a microtiter plate. They are then incubated overnight at 4° C. with 200 μl of a 1:1,000 dilution of the primary antiserum in PBS containing 0.05% Tween-20 (PBST) and 1% BSA. The plate containing the primary antibody is discarded, and the pin block is washed four times for 10 min each time with PBST. Then, peroxidase-conjugated secondary antibody (goat anti-human immunoglobulin M [IgM] or goat anti-human immunoglobulin G [IgG] at a 1:2,000 dilution in PBST plus 1% BSA) is added to the wells of a microtiter plate, and the pin block is inserted and incubated for 1 h at room temperature. After being washed as before, the block is inserted in a new microtiter plate containing 200 μl of o-phenylenediamine substrate per well and developed in the dark for 10 min with gentle agitation. Color development is stopped by the addition of 100 μl of 1 M H2SO4 per well, and the plate is read at 490 nm in a microplate reader.

A second PepSet will be constructed that include both a "window net" to further analyze the identified domains. The window net is performed to identify the precise boundaries of an identified epitope and consists of synthesizing all of the shorter overlapping sequences covering an identified antibody-binding peptide, which in this case are 4-mers, 5-mers-, 6-mers, and so on. The window net syntheses provide basic information on the location and boundaries of epitopes.

Patient sera will be tested against different OspC peptides on ELISA. A conserved OspC epitope, C10 peptide (PVVAESPKKP) (SEQ ID NO:8) at the C-terminal end of OspC and another peptide from a conserved region positions 9-22 consisting of 14 amino acid (ILMTLFLFISCNNS) (SEQ ID NO:9), together with additional OspC peptides from more variable regions identified with the Pepscan technology will be tested. Sera from patients from which the OspC1 and Ospc12 types as been determined by SSCP and sequencing will be used. We will also assess isolated IgM or IgG from these patient serum samples. We will isolate IgG from individual serum samples using Protein G affinity chromatography (Pierce Biotechnology, Inc., Rockford, Ill.). Unlike Protein A, Protein G binds all subclasses of human IgG and does not bind to human IgM. IgG will be eluted with 0.1 M glycine HCl (pH 2-3). IgM will be isolated using the Pierce Immobilized Mannan Binding Protein kit (Pierce Biotechnology, Inc., Rockford, Ill.) This way we will be able to determine the ability of each peptide to bind either IgM or IgG.

Because of the high variability of OspC some of the key epitopes of OspC may be genotype specific. If we find that one or more key epitopes are highly variable, we will expand our analysis to include additional genotypes of OspC, such as OspC2 and OspC10, targeting these variable regions. In addition, we will clone and express truncated portions of these genes and analyze the smaller proteins.

Comparable epitope mapping studies are done with the BBK32 protein of *Borrelia burgdorferi*. Example X lists some epitopes (peptides), selected from two fragments of the protein, that would be expected to bind specifically to an antibody against pathogenic *Borrelia*.

B. Cloning and Expression of Recombinant BBK32 and DbpA.

BBK32 and DbpA from *B. burgdorferi* strain B31 will be cloned according to the method developed by Heikkila et al. (2002) *Proc J. Clin. Micro.* 40, 453-460. The full sequences of bbk32 and dbpA from *B. burgdorferi* B31 are known (GenBank accession number AE000788 for bbk32 and AF069275 for dbpA). The bbk32 sequence predicts a protein of approximately 39 kD. The dbpA sequence predicts a protein of approximately 20 kD. PCR will be used to amplify the bbk32 and dbpA alleles from *B. burgdorferi* B31. Several primer pairs will be designed and tested to ensure that the entire coding sequence of both genes is obtained. The bbk32 and dbpA sequences will be generated by PCR amplification of *B. burgdorferi* genomic DNA. Approximately 1 ng of template DNA will be used under standard PCR conditions. The PCR-amplified full-length genes will be cloned into the pCR 2.1-TOPO plasmid vector (Invitrogen) for sequencing. DNA sequencing will be performed at UC Davis, Calif. To eliminate possible errors caused by Taq polymerase, the two strands of the genes will be sequenced independently. DNA and protein sequences will be analyzed with MacVector software.

The PCR-amplified gene of BBK32 (p35) and DbpA will be cloned into pET28a (Novagen) and will be transformed into *E. coli* BL21. Proteins will be purified via the histidine tag. The expression and purity of the rBBK32 and rDbpA proteins will be confirmed by sodium dodecyl sulfate (SDS)-polyacrylamide gel electrophoresis (PAGE). Purified protein will be used to generate mouse polyclonal antisera. This polyclonal sera will be used in Western Blot tests to evaluate BBK32 and DbpA antigenicity.

C. Epitope mapping of BBK32 and DpbA.

Analysis of continuous B-cell epitopes will be carried out by means of the Multipin Peptide Technology (PepScan) of Chiron Mimotopes (San Diego, Calif.) in a similar way as described above for OspC. The amino acid sequence will be used to synthesize a complete set of overlapping dodecapeptides. These will be covalently attached to the surfaces of derivatized polyethylene pins in a format compatible with standard enzyme-linked immunosorbent assays (ELISAs). These overlapping peptides will cover the entire protein. The reactivity of pooled sera from 20 patients with culture confirmed Lyme disease with the pin-bound peptides will be detected by a modified enzyme immunoassay.

Because of the higher variability of OspC some of the key epitopes of OspC may be genotype specific. If we find that one or more key epitopes are highly variable, we will expand our analysis to include additional genotypes of OspC, such as OspC2 and OspC10, targeting these variable regions. In addition, we will clone and express truncated portions of these genes and analyze the smaller proteins.

Example VIII

Evaluating the Ability of Peptides Containing Epitopes as Identified in Example VI to Bind Anti-*B. Burgdorferi* IgM and IgG Antibodies We will use serum and isolated IgG and IgM from patients with culture confirmed early LD to assess the diagnostic potential of OspC1, OspC12, BBK32 and DbpA epitopes in synthetic peptides. The peptide synthesis and ELISA methods that we will use are described in Example I. WE expect that it is unlikely that only one OspC or BBK32 peptide will provide sufficient sensitivity to identify individuals with antibodies to either protein. We plan to assess peptides containing epitopes from different regions of each protein. We will use 50 serum samples from patients with culture confirmed early LD, 50 serum samples from patients with culture confirmed acute disseminated LD, 50 serum sample from patients with late LD, 50 serum from a bank of normal health patients from endemic and non endemic areas, and panels of serum from other tick borne and diseases that are in the differential diagnosis of LD. These latter panels will include serum from 20 patients with rheumatoid arthritis, 20 patients with SLE, 20 patients with syphilis, 20 patients with MS, 20 patients with

*H. pylori*, 20 patients with culture confirmed HGE and 20 patients with microbiologically confirmed babesiosis. Other antigens recognized early in the course of infection, such as p37 and p39, will also be cloned and scanned.

Example IX

Developing an Immunodiagnostic Peptide Assay

Initially, an ELISA test will be developed followed by an assay developed on a membrane (rapid format). Later, we will compare the sensitivity and specificity of the prototype assay to whole *B. burgdorferi* antigen ELISA and western blot (CDC two-tiered system).

A. Selection of the Peptides: the selection will be based on 1) additional tests of the sensitivity and specificity of each peptide (e.g. using sera from patients who have been infected with other organisms known to have cross-reactivity with *B. burgdorferi*); 2) the relative coating efficiency of each peptide combination (see below).

B. Preparation and Testing of Microwells Coated with Peptides.

We have found, unexpectedly, that synthetic IR6 peptides down to even 16-17 residues are adsorbed to microwell surfaces quite well without the need for biotinylation and linking to streptavidin, and that the directly adsorbed peptides were as efficient as the streptavidin-conjugated antigens for ELISA detection of *B. burgdorferi* antibodies. The free peptides were not, however, well adsorbed on nitrocellulose surfaces for use in Fast Format (lateral flow) immunoassays. We found that direct biotinylation of synthetic peptides at the N-terminus during solid-phase synthesis was much more convenient than linking biotinyl groups to free peptides after deprotection and cleavage from the solid supports. Also, streptavidin conjugates of N-biotinylated peptides worked as well in the Rapid Format assays as did the peptides linked to streptavidin according to the published protocol (Liang et al. (1999a) (supra)

Since we will synthesize some small peptides encompassing single linear epitopes, in general all peptides will be synthesized with N-terminal biotinyl residues and streptavidin conjugates will be used for both ELISA and Rapid Format (membrane) assays. With the biotinyl groups attached during the solid phase synthesis, conjugation with streptavidin is hardly more complicated than coating plates with free peptides, and there will be no worry about poor adhesion of short peptides to the immobilizing surfaces. The peptides do not need to be immobilized in a specific ratio to one another, but enough of each peptide must be bound to ensure that none of the epitopes becomes limiting in ELISA assays of patient sera.

C. Comparison of Prototype Peptide Assay to whole *B. Burgdorferi* Elisa and Western Blot.

Once we have identified the best peptide combination(s), we will compare the prototype peptide assay to the standard CDC recommended protocol. The clinical samples will be run on a standard ELISA using whole low passage *B. burgdorferi* and on IgM and IgG western blots to compare the results of the peptide assay.

Positive Controls: Recombinant proteins OspC, FlaB, BBK32, DbpA and the full length IR6 peptide will be used as controls. The reactivity of each of the peptides will be compared to the corresponding recombinant protein.

Negative Controls: To assess non-specific binding of antibodies in our peptide assay we will use a specifically designed random peptide. To assess non-specific binding of antibodies in our recombinant protein positive control assay we will use BSA.

Positive serum samples to be used to assess peptide preparations and comparative proteins:

a. 100 serum samples obtained at presentation from patients with culture confirmed early local LD.
b. 100 serum samples obtained at presentation from patients with culture confirmed acute disseminated LD.
c. 100 serum sample from patients with late LD.

Negative control serum samples to be used to assess peptide preparations and comparative proteins:

a. 100 sera from a bank of normal health patients from endemic areas.
b. 100 sera from a bank of normal health patients from non-endemic areas.
c. 50 sera samples from individual patients with culture confirmed HGE.
d. 20 sera samples from individual patients with microbiologically confirmed babesiosis.
e. 50 sera samples from individual patients with rheumatoid arthritis
f. 30 sera samples from individual patients with SLE.
g. 50 sera samples from individual patients with syphilis.
h. 50 sera samples from individual patients with MS.
i. 50 sera samples from individual patients with *H. pylori.*

It is expected that the peptides tested will provide a sensitive, specific assay which is at least as effective as the presently approved C6 assay.

Example X

Preparation and Characterization of Multi-epitope Polypeptides

In order to significantly increase the sensitivity of the IR6-based peptide assay, we constructed multimeric peptides (dimers and trimers) containing epitopes from VlsE-IR6, Fla (p41) and OspC and compared them to the IR6-25 and the IR6-17 residue peptides. The epitopes used were as follows: the IR6-17 residue peptide is MKKDDQIAAAIALRGMA (SEQ ID NO:1); the IR6-25 peptide is MKKDDQIAAAIALRGMAKDGKFAVK (SEQ ID NO:20); the Flap$41_{13}$ peptide is VQEGVQQEGAQQP (SEQ ID NO:18); and the $pepC_{10}$ peptide is PVVAESPKKP (SEQ ID NO:8). A spacer of 3 glycines was inserted between the epitopes in each dimer or trimer.

The sequences of the peptides tested is:

1. $FLA_{13}$-$IR6_{17}$-$PepC_{10}$ (47 mer)
Biotin-V-Q-E-G-V-Q-Q-E-G-A-Q-Q-P-G-G-G-M-K-K-D-D-Q-I-A-A-A-I-A-L-R-G-M-A-G-G-G-P-V-V-A-E-S-P-K-K-P-amide (SEQ ID NO: 21)

2. $FLA_{13}$-$IR6_{17}$ (34 mer)
Biotin-V-Q-E-G-V-Q-Q-E-G-A-Q-Q-P-G-G-G-M-K-K-D-D-Q-I-A-A-A-I-A-L-R-G-M-A-amide (SEQ ID NO: 22)

-continued

3. IR6₁₇-PepC₁₀ (31 mer)
Biotin-M-K-K-D-D-Q-I-A-A-A-I-A-L-R-G-M-A-G-G-G-P-V-V-A-E-S-P-K-K-P-amide        (SEQ ID NO: 23)

4. PepC₁₀-IR6₁₇ (31 mer)
Biotin-P-V-V-A-E-S-P-K-K-P-G-G-G-M-K-K-D-D-Q-I-A-A-A-I-A-L-R-G-M-A-amide        (SEQ ID NO: 24)

5. IR6₁₇-FLA₁₃ (34 mer)
Biotin-M-K-K-D-D-Q-I-A-A-A-I-A-L-R-G-M-A-G-G-G-V-Q-E-G-V-Q-Q-E-G-A-Q-Q-P-amide  (SEQ ID NO: 25)

6. B31 (25 mer)
Biotin-M-K-K-D-D-Q-I-A-A-A-I-A-L-R-G-M-A-K-D-G-K-F-A-V-K-amide                  (SEQ ID NO: 20)

7. B31 (17 mer)
Biotin-M-K-K-D-D-Q-I-A-A-A-I-A-L-R-G-M-A-amide                                  (SEQ ID NO: 1)

8. FLA₁₃-modif*52IR6₁₈-pepC10 (47 mer)
acetyl-V-Q-E-G-V-Q-Q-E-G-A-Q-Q-P-G-G-G-M-K-K-N-D-K-I-A-A-A-I-A-L-R-G-M-G-G-G-G-P-  (SEQ ID NO: 59)
V-V-A-E-S-P-K-K-P-amide 9. FLA₁₃-modif*52IR6₁₈-pepC10 (47 mer)
acetyl-C-V-Q-E-G-V-Q-Q-E-G-A-Q-Q-P-G-G-G-M-K-K-N-D-K-I-A-A-A-I-A-L-R-G-M-G-G-G-  (SEQ ID NO: 60)
G-P-V-V-A-E-S-P-K-K-P-amide 10. FLA₁₃-modif*53IR6₁₈-pepC10 (47 mer)
acetyl-V-Q-E-G-V-Q-Q-E-G-A-Q-Q-P-G-G-G-M-K-K-N-D-Q-I-G-A-A-I-A-L-R-G-M-V-G-G-G-P-  (SEQ ID NO: 61)
V-V-A-E-S-P-K-K-P-amide 11. FLA₁₃-modif*43IR6₁₈-pepC10 (47 mer)
acetyl-V-Q-E-G-V-Q-Q-E-G-A-Q-Q-P-G-G-G-M-K-K-N-D-K-I-A-A-A-I-V-L-R-G-V-A-G-G-G-P-  (SEQ ID NO: 62)
V-V-A-E-S-P-K-K-P-amide 12. FLA₁₃-modif*51IR6₁₈-pepC10 (47 mer)
acetyl-V-Q-E-G-V-Q-Q-E-G-A-Q-Q-P-G-G-G-G-M-K-K-N-D-Q-I-V-A-A-I-A-L-R-G-M-V-G-P-  (SEQ ID NO: 63)
V-V-A-E-S-P-K-K-P-amide We used a panel of 6 well defined clinically characterized and culture positive Lyme disease sera that were previously tested by ELISA: two low, two medium and two high titer from six different Lyme patients, in addition to one negative control obtained from an healthy individual. The data are shown in FIG. 1. We observed that the multimeric peptides Fla₁₃-IR6₁₇-PepC₁₀, Fla₁₃-IR6₁₇ and PepC₁₀-IR6₁₇ detected both low titer LD samples, in contrast to the IR6 standards (IR6-25mer and IR6-17mer), which detected only one sample of the two. The other two combinations tested (IR6₁₇-PepC₁₀ and IR6₁₇-Fla₁₃) had equivalent sensitivity to the standards (IR6-25 and IR6-17). These results indicate that the multimeric peptides (Fla₁₃-IR6₁₇-PepC₁₀, Fla₁₃-IR6₁₇ and PepC₁₀-IR6₁₇) detect anti-Borrelia antibodies with superior sensitivity than the standard based on single IR6 peptides. This indicates that combinations of peptides in a single fusion peptide can increase the sensitivity of the assay.

The results of the studies with the trimer represented by SEQ ID NO:59 are shown in Tables 8 and 9:

TABLE 8

Dog sera versus trimer represented by SEQ ID NO:59
(18-mer of previous studies replaced with the trimer of *52)

|  | n | C6 Assay | N. Pos./Total (%) 26 mer B31 | new trimer *52 |
| --- | --- | --- | --- | --- |
| Lyme Disease (Dog) | 37 | ND | 29 78.30% | 30 81% |
| Healthy Controls | 9 | ND | 0 0% | 0 0% |

Conclusion: Dog American sera is equivalent between this trimer and 26-mer B31. C6 was not tested.

TABLE 9

Human American sera versus trimer represented by SEQ ID NO:59

|  | n | C6 assay | N. Pos./Total (%) 26mer B31 | new trimer*52 |
| --- | --- | --- | --- | --- |
| Early LD (Human american P2 panel, StonyBrook) | 27 | 18 67% | 22 81.50% | 20 74% |

Conclusion: this trimer is much better than 26merPT7(C6assay) as is equivalent to 26mer B31 as for dog sera.

The trimers represented by SEQ ID NOs:60 through 63 are expected to give results similar to those obtained with the trimer of SEQ ID NO:59.

In a further experiment, the trimer represented by SEQ ID NO:47 was further tested with respect to its ability to detect IgM antibodies, compared to the primer of the commercially available C6 assay (26-mer PT7). The results, as shown below, indicate that the primer is statistically significantly more effective than is the commercially available primer, when tested in this manner.

|  | 26-mer PT7 | 26-mer B31 | SEQ ID NO: 47 |
| --- | --- | --- | --- |
| TOTAL | 18/40 (45%) | 21/40 (53%) | 29/40 (72.5%) |

Other multi-epitope polypeptides that would be expected to show high sensitivity in an assay of the invention include polypeptides that contain, in addition to an IR6₁₇ epitope, an epitope from BBK32 (a fibronectin binding protein of *Borrelia burgdorferi*). Among the single BBK32 peptides that are effective are the following peptides:

Peptides from Fragment 1:

BBK32$_{23-43}$ (21 mer):
(SEQ ID NO: 26)
biotin-F-I-R-Y-E-M-K-E-E-S-P-G-L-F-D-K-G-N-S-I-L-amide BBK32$_{49-78}$ (30 mer):
(SEQ ID NO: 27)
biotin-S-I-K-K-P-M-N-K-K-G-K-G-K-I-A-R-K-K-G-K-S-K-V-S-R-K-E-P-Y-I-amide BBK32$_{77-93}$ (17 mer):
(SEQ ID NO: 28)
biotin-Y-I-H-S-L-K-R-D-S-A-N-K-S-N-F-L-Q-amide Peptides from Fragment 2:

BBK32$_{118-140}$ (23 mer):
(SEQ ID NO: 29)
biotin-K-I-Q-K-Q-Q-D-E-Y-K-G-M-T-Q-G-S-L-N-S-L-S-G-E-amide BBK32$_{157-185}$ (29 mer):
(SEQ ID NO: 30)
biotin-I-D-S-D-L-R-P-K-S-S-L-Q-D-I-A-G-S-N-S-I-S-Y-T-D-E-I-E-E-E-amide BBK32$_{187-208}$ (22 mer):
(SEQ ID NO: 31)
biotin-Y-A-R-Y-Y-L-D-E-D-D-E-D-D-E-Y-Y-E-D-D-Y-E-E-amide BBK32$_{207-231}$ (25 mer):
(SEQ ID NO:32)
biotin-E-E-I-R-L-S-N-R-Y-Q-S-Y-L-E-G-V-K-Y-N-V-D-S-A-I-N-amide Some suitable multi-epitope peptides containing an IR6$_{17}$ epitope and an epitope from BBK32 include:

FLA$_{13}$-IR6$_{17}$-BBK32$_9$ (46 mer)
Biotin-V-Q-E-G-V-Q-Q-E-G-A-Q-Q-P-G-G-G-M-K-K-D-D-Q-I-A-A-A-I-A-L-R-G-M-A-G-G-G-S-D-L-R-P-K-S-S-L-amide     (SEQ ID NO: 33)

FLA$_{13}$-IR6$_{17}$-BBK32$_{10}$ (47 mer)
Biotin-V-Q-E-G-V-Q-Q-E-G-A-Q-Q-P-G-G-G-M-K-K-D-D-Q-I-A-A-A-I-A-L-R-G-M-A-G-G-G-I-R-L-S-N-R-Y-Q-S-Y-amide     (SEQ ID NO: 34)

FLA$_{13}$-IR6$_{17}$-BBK32$_{11}$ (48 mer)
Biotin-V-Q-E-G-V-Q-Q-E-G-A-Q-Q-P-G-G-G-M-K-K-D-D-Q-I-A-A-A-I-A-L-R-G-M-A-G-G-G-Y-L-D-E-D-D-E-D-D-E-Y-amide     (SEQ ID NO: 35)

BBK32$_{17}$-IR6$_{17}$ (37mer)
biotin-Y-L-D-E-D-D-E-D-D-E-Y-Y-E-D-D-Y-E-G-G-G-M-K-K-D-D-Q-I-A-A-A-I-A-L-R-G-M-A-amide     (SEQ ID NO: 36)

PepC10-FLA$_{13}$-IR6$_{17}$ (47mer)
Biotin-P-V-V-A-E-S-P-K-K-P-G-G-G-V-Q-E-G-V-Q-Q-E-G-A-Q-Q-P-G-G-G-M-K-K-D-D-Q-I-A-A-A-I-A-L-R-G-M-A-amide     (SEQ ID NO: 37)

FLA$_{13}$-PepC$_{10}$-IR6$_{17}$ (47mer)
Biotin-V-Q-E-G-V-Q-Q-E-G-A-Q-Q-P-G-G-G-P-V-V-A-E-S-P-K-K-P-G-G-G-M-K-K-D-D-Q-I-A-A-A-I-A-L-R-G-M-A-amide     (SEQ ID NO: 38)

Example XI

Peptides Containing Additional Substituted Amino Acids

We compared peptides from *B. burgdorferi* (B31-17) and *B. garinii* (IP90-17) to a series of newly constructed peptides having substituted amino acids at one or more of positions 4, 6, 8, 11, 12, 16 or 17 of SEQ ID NO:1. The tested peptides include many of those listed below. All of these tested peptides contained an added N-terminal cysteine, so they are referred to here as IR6 18-mer peptides.

| Sequence | Source | SEQ ID NO |
|---|---|---|
| CMKKDDQIAAAIALRGMA | B31 (*B. burgdorferi*) | (SEQ ID NO: 19) |
| CMKKDDQIAAAMVLRGMA | IP90 (*B. garinii*) | (SEQ ID NO: 51) |
| CMKKRNDNIAAAIVLRGVA | ***89 (*B. afzelii* p5) | (SEQ ID NO: 52) |
| CMKKNDKIAAAIALRGMV | ***84 | (SEQ ID NO: 53) |
| CMKKNDKIAAA<u>I</u>VLRGVA | ***43 | (SEQ ID NO: 54) |
| CMKKNDQIVAAIALRGMV | ***51 | (SEQ ID NO: 55) |

```
                    -continued
CMKKNDKIAAAIALRGMG    ***52          (SEQ ID NO: 56)

CMKKNDQIGAAIALRGMV    ***53          (SEQ ID NO: 57)

CMKKNDQIGAAIALRGMG    ***54          (SEQ ID NO: 58)
```

We assessed sensitivity using serum obtained from dogs living in the Northeastern United States with suspected Lyme disease and from normal healthy dogs (Table 10) and two panels of clinically defined human Lyme disease sera, one from the United States (Table 11) and the other from Bulgaria (Table 12). European patients can be infected with any one of the pathogenic genospecies, while *B. burgdorferi* is the only pathogenic genospecies in North America.

We tested these peptides in a standard ELISA using methods previously described (e.g., in Example I. The sera used were from well characterized patient samples, including from patients with early Lyme disease with erythema migrans, and acute disseminated Lyme disease. As controls, we used sera from normal healthy adults.

TABLE 10

Comparison between eight IR6 18-mer peptides for sensitivity in dog samples from North Eastern United States

| Peptide | B31 | IP90 (C6) | ***84 | ***43 | ***51 | ***52 | ***53 | ***54 |
|---|---|---|---|---|---|---|---|---|
| Illness compatible with LD. Bands on WB (n = 20) | 12P (60%) | 12P (60%) | 10P (50%) | 13P (65%) | 13P (65%) | 15P (75%) | 12P (60%) | 10P (50%) |
| Healthy Dogs WB negative (n = 12) | 0 | 0 | 0 | 0 | 0 | 0 | 0 | 0 |

P = Positive
The cut-off is calculated on all 12 negative controls (Mean + 3 SD):

TABLE 11

Comparison between five IR6 18-mer peptides for sensitivity in American patients presenting with erythema migrans.

| Peptide | C6 No. Pos/ Total (%) | ***51 No. Pos/ Total (%) | ***52 No. Pos/ Total (%) | ***53 No.Pos/ Total (%) | ***89 No. Pos/ Total (%) |
|---|---|---|---|---|---|
| EM patients N = 27 | 12/27 (44%) | 12/27 (44%) | 12/27 44%) | 11/27 (41%) | 12/27 (44%) |
| Normal Controls N = 7 | 0/7 | 0/7 | 0/7 | 0/7 | 0/7 |

TABLE 12

Comparison between five IR6 18-mer peptides for sensitivity in European (Bulgarian) patients presenting with erythema migrans.

| Peptide | C6 No. Pos/ Total (%) | ***52 No. Pos/ Total (%) | ***89 No. Pos/ Total (%) | ***43 No. Pos/ Total (%) |
|---|---|---|---|---|
| EM patients N = 19 | 10/19 (53%) | 12/19 (63%) | 10/19 (53%) | 12/19 (63%) |

TABLE 12-continued

Comparison between five IR6 18-mer peptides for sensitivity in European (Bulgarian) patients presenting with erythema migrans.

| Peptide | C6 No. Pos/ Total (%) | ***52 No. Pos/ Total (%) | ***89 No. Pos/ Total (%) | ***43 No. Pos/ Total (%) |
|---|---|---|---|---|
| Normal Controls N = 7 | 0/7 | 0/7 | 0/7 | 0/7 |

These data show that changes at the indicated positions can improve the ability of a peptide of the invention to bind antibody from divergent species. It is expected that peptides having other changes at these positions will exhibit similar specificities. Furthermore, it is expected that such altered peptides, when tested for sensitivity as shown in Example IV, will also exhibit the desired degree of sensitivity for use in an assay of the invention.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. provisional applications 60/779,016, filed May 10, 2006 and 60/875,820, filed Dec. 20, 2006, and PCT/US2007/011289, filed Mar. 13, 2008, and in the FIGURES, are hereby incorporated in their entirety by reference.

We claim:

1. An isolated peptide comprising the sequence MKKNDQI(V or G)AAIALRGVA (SEQ ID NO:64), wherein the peptide is no longer than 24 amino acids, and wherein the peptide can bind specifically to an antibody against a pathogenic *Borrelia*.

2. The isolated peptide of claim 1, wherein the peptide comprises the sequence

MKKNDQIVAAIALRGVA (SEQ ID NO: 65) or

MKKNDQIGAAIALRGVA (SEQ ID NO: 66).

3. The isolated peptide of claim 1, which consists of the sequence

MKKNDQI(V or G)AAIALRGVAK (SEQ ID NO: 73),

MKKNDQI(V or G)AAIALRGVAKD (SEQ ID NO: 74),

MKKNDQI(V or G)AAIALRGVAKDG (SEQ ID NO: 75),

MKKNDQI(V or G)AAIALRGVAKDGK (SEQ ID NO: 76),

MKKNDQI(V or G)AAIALRGVAKDGKF (SEQ ID NO: 77),

MKKNDQI(V or G)AAIALRGVAKDGKFA (SEQ ID NO: 78), or

MKKNDQI(V or G)AAIALRGVAKDGKFAV (SEQ ID NO: 79).

4. The isolated peptide of claim 1, which consists of the sequence

MKKNDQIVAAIALRGVA (SEQ ID NO: 65) or

MKKNDQIGAAIALRGVA (SEQ ID NO: 66), or which consists of the sequence of SEQ ID NO:65 or SEQ ID NO:66 plus an N-terminal C residue, which are SEQ ID NO:80 or SEQ ID NO:81, respectively.

5. A composition comprising an isolated peptide of claim 1 and one or more additional peptides which are specific for antibodies against the same or a different protein of the same or a different pathogenic *Borrelia*.

6. A diagnostic reagent comprising an isolated peptide of claim 1 and a system for detecting the peptide and/or a substrate for immobilizing the peptide.

7. A kit for diagnosing Lyme borreliosis, comprising an isolated peptide of claim 1, and a system for detecting the peptide bound to an antibody to a pathogenic *Borrelia* protein and/or a substrate for immobilizing the peptide.

8. An isolated compound comprising the peptide of claim 1 linked to at least one further moiety, via a terminal amino acid linker or a chemical coupling agent.

9. The isolated compound of claim 8, wherein the at least one further moiety is a second peptide that specifically recognizes an antibody against a pathogenic *Borrelia*, wherein the peptide and the second peptide are covalently linked.

10. The isolated compound of claim 8, wherein the sequence of the peptide, including the further moiety, comprises VQEGVQQEGAQQPGGGMKKNDQI(V or G)AAIALRGVA (SEQ ID NO:68).

11. The isolated compound of claim 8, wherein the sequence of the peptide, including the further moiety, consists of VQEGVQQEGAQQPGGGMKKNDQIVAAIALRGVA (SEQ ID NO:69) or CVQEGVQQEGAQQPGGGMKKNDQIVAAIALRGVA (SEQ ID NO:70).

12. The isolated compound of claim 8, wherein the sequence of the peptide, including the further moiety, consists of VQEGVQQEGAQQPGGGMKKNDQIGAAIALRGVA (SEQ ID NO:71) or CVQEGVQQEGAQQPGGGMKKNDQIGAAIALRGVA (SEQ ID NO:72).

13. The isolated compound of claim 9, wherein the peptide and the second peptide are separated from one another by a spacer of one to five Glycine or Alanine residues.

14. The isolated compound of claim 9, wherein the second peptide comprises an epitope from *Borrelia* flagellin p41 or from *Borrelia* OspC.

15. The isolated compound of claim 14, wherein the epitope from flagellin p41 has the sequence VQEGVQQEGAQQP (SEQ ID NO:18), or the epitope from OspC has the sequence PVVAESPKKP (SEQ ID NO:8).

16. A method for diagnosing Lyme disease in a subject, comprising contacting a sample from a subject suspected of having antibodies against a causative agent of Lyme disease with an isolated peptide of claim 1, under conditions effective for the formation of a peptide-antibody complex, and detecting the presence of the peptide-antibody complex.

17. The method of claim 16, wherein the peptide-antibody complex is detected by adding a binding partner which is labeled, or which can be labeled with a signal generating reagent.

18. The method of claim 17, wherein the binding partner is an antibody attached to an enzyme, and a signal is generated when the enzyme reacts with a suitable substrate.

19. The method of claim 16, wherein the detecting is performed with an ELISA assay.

20. The method of claim 16, wherein the subject is a cat or a dog.

21. The method of claim 16, wherein the subject is a human.

* * * * *

SEQUENCE LISTING

<160> NUMBER OF SEQ ID NOS: 81

<210> SEQ ID NO 1
<211> LENGTH: 17
<212> TYPE: PRT
<213> ORGANISM: Borrelia sp.

<400> SEQUENCE: 1

Met Lys Lys Asp Asp Gln Ile Ala Ala Ala Ile Ala Leu Arg Gly Met
1               5                   10                  15

Ala

<210> SEQ ID NO 2
<211> LENGTH: 26
<212> TYPE: PRT
<213> ORGANISM: Borrelia sp.

<400> SEQUENCE: 2

Cys Met Lys Lys Asp Asp Gln Ile Ala Ala Ala Met Val Leu Arg Gly
1               5                   10                  15

Met Ala Lys Asp Gly Gln Phe Ala Leu Lys
            20                  25

<210> SEQ ID NO 3
<211> LENGTH: 26
<212> TYPE: PRT
<213> ORGANISM: Borrelia sp.

<400> SEQUENCE: 3

Cys Met Lys Lys Asp Asp Gln Ile Ala Ala Ala Ile Ala Leu Arg Gly
1               5                   10                  15

Met Ala Lys Asp Gly Lys Phe Ala Val Lys
            20                  25

<210> SEQ ID NO 4
<211> LENGTH: 18
<212> TYPE: PRT
<213> ORGANISM: Borrelia sp.

<400> SEQUENCE: 4

Met Lys Lys Asp Asp Gln Ile Ala Ala Ala Ile Ala Leu Arg Gly Met
1               5                   10                  15

Ala Lys

<210> SEQ ID NO 5
<211> LENGTH: 16
<212> TYPE: PRT
<213> ORGANISM: Borrelia sp.

<400> SEQUENCE: 5

Met Lys Lys Asp Asp Gln Ile Ala Ala Ala Ile Ala Leu Arg Gly Met
1               5                   10                  15

<210> SEQ ID NO 6
<211> LENGTH: 17
<212> TYPE: PRT
<213> ORGANISM: Borrelia sp.

<400> SEQUENCE: 6

Met Lys Lys Asp Asp Gln Ile Ala Ala Ala Met Val Leu Arg Gly Met
1               5                   10                  15

Ala

<210> SEQ ID NO 7
<211> LENGTH: 16
<212> TYPE: PRT
<213> ORGANISM: Borrelia sp.

<400> SEQUENCE: 7

Lys Lys Asp Asp Gln Ile Ala Ala Ala Ile Ala Leu Arg Gly Met Ala
 1               5                  10                  15

<210> SEQ ID NO 8
<211> LENGTH: 10
<212> TYPE: PRT
<213> ORGANISM: Borrelia sp.

<400> SEQUENCE: 8

Pro Val Val Ala Glu Ser Pro Lys Lys Pro
 1               5                  10

<210> SEQ ID NO 9
<211> LENGTH: 14
<212> TYPE: PRT
<213> ORGANISM: Borrelia sp.

<400> SEQUENCE: 9

Ile Leu Met Thr Leu Phe Leu Phe Ile Ser Cys Asn Asn Ser
 1               5                  10

<210> SEQ ID NO 10
<211> LENGTH: 17
<212> TYPE: PRT
<213> ORGANISM: Borrelia sp.

<400> SEQUENCE: 10

Met Lys Lys Asn Asp Gln Ile Ala Ala Ala Ile Val Leu Arg Gly Met
 1               5                  10                  15

Ala

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 11

His His His His His His
 1               5

<210> SEQ ID NO 12
<211> LENGTH: 19
<212> TYPE: PRT
<213> ORGANISM: Borrelia sp.

<400> SEQUENCE: 12

Met Lys Lys Asp Asp Gln Ile Ala Ala Ala Ile Ala Leu Arg Gly Met
 1               5                  10                  15

Ala Lys Asp

<210> SEQ ID NO 13
<211> LENGTH: 20

```
<212> TYPE: PRT
<213> ORGANISM: Borrelia sp.

<400> SEQUENCE: 13

Met Lys Lys Asp Asp Gln Ile Ala Ala Ala Ile Ala Leu Arg Gly Met
 1               5                  10                  15

Ala Lys Asp Gly
            20

<210> SEQ ID NO 14
<211> LENGTH: 21
<212> TYPE: PRT
<213> ORGANISM: Borrelia sp.

<400> SEQUENCE: 14

Met Lys Lys Asp Asp Gln Ile Ala Ala Ala Ile Ala Leu Arg Gly Met
 1               5                  10                  15

Ala Lys Asp Gly Lys
            20

<210> SEQ ID NO 15
<211> LENGTH: 22
<212> TYPE: PRT
<213> ORGANISM: Borrelia sp.

<400> SEQUENCE: 15

Met Lys Lys Asp Asp Gln Ile Ala Ala Ala Ile Ala Leu Arg Gly Met
 1               5                  10                  15

Ala Lys Asp Gly Lys Phe
            20

<210> SEQ ID NO 16
<211> LENGTH: 23
<212> TYPE: PRT
<213> ORGANISM: Borrelia sp.

<400> SEQUENCE: 16

Met Lys Lys Asp Asp Gln Ile Ala Ala Ala Ile Ala Leu Arg Gly Met
 1               5                  10                  15

Ala Lys Asp Gly Lys Phe Ala
            20

<210> SEQ ID NO 17
<211> LENGTH: 24
<212> TYPE: PRT
<213> ORGANISM: Borrelia sp.

<400> SEQUENCE: 17

Met Lys Lys Asp Asp Gln Ile Ala Ala Ala Ile Ala Leu Arg Gly Met
 1               5                  10                  15

Ala Lys Asp Gly Lys Phe Ala Val
            20

<210> SEQ ID NO 18
<211> LENGTH: 13
<212> TYPE: PRT
<213> ORGANISM: Borrelia sp.

<400> SEQUENCE: 18

Val Gln Glu Gly Val Gln Gln Glu Gly Ala Gln Gln Pro
 1               5                  10
```

```
<210> SEQ ID NO 19
<211> LENGTH: 18
<212> TYPE: PRT
<213> ORGANISM: Borrelia sp.

<400> SEQUENCE: 19

Cys Met Lys Lys Asp Asp Gln Ile Ala Ala Ala Ile Ala Leu Arg Gly
 1               5                  10                  15
Met Ala

<210> SEQ ID NO 20
<211> LENGTH: 25
<212> TYPE: PRT
<213> ORGANISM: Borrelia sp.

<400> SEQUENCE: 20

Met Lys Lys Asp Asp Gln Ile Ala Ala Ala Ile Ala Leu Arg Gly Met
 1               5                  10                  15
Ala Lys Asp Gly Lys Phe Ala Val Lys
            20                  25

<210> SEQ ID NO 21
<211> LENGTH: 46
<212> TYPE: PRT
<213> ORGANISM: Borrelia sp.

<400> SEQUENCE: 21

Val Gln Glu Gly Val Gln Gln Glu Gly Ala Gln Gln Pro Gly Gly Gly
 1               5                  10                  15
Met Lys Lys Asp Asp Gln Ile Ala Ala Ala Ile Ala Leu Arg Gly Met
            20                  25                  30
Ala Gly Gly Gly Pro Val Val Ala Glu Ser Pro Lys Lys Pro
        35                  40                  45

<210> SEQ ID NO 22
<211> LENGTH: 33
<212> TYPE: PRT
<213> ORGANISM: Borrelia sp.

<400> SEQUENCE: 22

Val Gln Glu Gly Val Gln Gln Glu Gly Ala Gln Gln Pro Gly Gly Gly
 1               5                  10                  15
Met Lys Lys Asp Asp Gln Ile Ala Ala Ala Ile Ala Leu Arg Gly Met
            20                  25                  30
Ala

<210> SEQ ID NO 23
<211> LENGTH: 30
<212> TYPE: PRT
<213> ORGANISM: Borrelia sp.

<400> SEQUENCE: 23

Met Lys Lys Asp Asp Gln Ile Ala Ala Ala Ile Ala Leu Arg Gly Met
 1               5                  10                  15
Ala Gly Gly Gly Pro Val Val Ala Glu Ser Pro Lys Lys Pro
            20                  25                  30

<210> SEQ ID NO 24
<211> LENGTH: 30
<212> TYPE: PRT
<213> ORGANISM: Borrelia sp.
```

```
<400> SEQUENCE: 24

Pro Val Val Ala Glu Ser Pro Lys Lys Pro Gly Gly Gly Met Lys Lys
 1               5                  10                  15

Asp Asp Gln Ile Ala Ala Ala Ile Ala Leu Arg Gly Met Ala
            20                  25                  30

<210> SEQ ID NO 25
<211> LENGTH: 33
<212> TYPE: PRT
<213> ORGANISM: Borrelia sp.

<400> SEQUENCE: 25

Met Lys Lys Asp Asp Gln Ile Ala Ala Ala Ile Ala Leu Arg Gly Met
 1               5                  10                  15

Ala Gly Gly Gly Val Gln Glu Gly Val Gln Gln Glu Gly Ala Gln Gln
            20                  25                  30

Pro

<210> SEQ ID NO 26
<211> LENGTH: 21
<212> TYPE: PRT
<213> ORGANISM: Borrelia sp.

<400> SEQUENCE: 26

Phe Ile Arg Tyr Glu Met Lys Glu Glu Ser Pro Gly Leu Phe Asp Lys
 1               5                  10                  15

Gly Asn Ser Ile Leu
            20

<210> SEQ ID NO 27
<211> LENGTH: 30
<212> TYPE: PRT
<213> ORGANISM: Borrelia sp.

<400> SEQUENCE: 27

Ser Ile Lys Lys Pro Met Asn Lys Lys Gly Lys Gly Lys Ile Ala Arg
 1               5                  10                  15

Lys Lys Gly Lys Ser Lys Val Ser Arg Lys Glu Pro Tyr Ile
            20                  25                  30

<210> SEQ ID NO 28
<211> LENGTH: 17
<212> TYPE: PRT
<213> ORGANISM: Borrelia sp.

<400> SEQUENCE: 28

Tyr Ile His Ser Leu Lys Arg Asp Ser Ala Asn Lys Ser Asn Phe Leu
 1               5                  10                  15

Gln

<210> SEQ ID NO 29
<211> LENGTH: 23
<212> TYPE: PRT
<213> ORGANISM: Borrelia sp.

<400> SEQUENCE: 29

Lys Ile Gln Lys Gln Gln Asp Glu Tyr Lys Gly Met Thr Gln Gly Ser
 1               5                  10                  15

Leu Asn Ser Leu Ser Gly Glu
            20
```

```
<210> SEQ ID NO 30
<211> LENGTH: 29
<212> TYPE: PRT
<213> ORGANISM: Borrelia sp.

<400> SEQUENCE: 30

Ile Asp Ser Asp Leu Arg Pro Lys Ser Ser Leu Gln Asp Ile Ala Gly
 1               5                  10                  15

Ser Asn Ser Ile Ser Tyr Thr Asp Glu Ile Glu Glu Glu
            20                  25

<210> SEQ ID NO 31
<211> LENGTH: 22
<212> TYPE: PRT
<213> ORGANISM: Borrelia sp.

<400> SEQUENCE: 31

Tyr Ala Arg Tyr Tyr Leu Asp Glu Asp Glu Asp Asp Glu Tyr Tyr
 1               5                  10                  15

Glu Asp Asp Tyr Glu Glu
            20

<210> SEQ ID NO 32
<211> LENGTH: 25
<212> TYPE: PRT
<213> ORGANISM: Borrelia sp.

<400> SEQUENCE: 32

Glu Glu Ile Arg Leu Ser Asn Arg Tyr Gln Ser Tyr Leu Glu Gly Val
 1               5                  10                  15

Lys Tyr Asn Val Asp Ser Ala Ile Asn
            20                  25

<210> SEQ ID NO 33
<211> LENGTH: 45
<212> TYPE: PRT
<213> ORGANISM: Borrelia sp.

<400> SEQUENCE: 33

Val Gln Glu Gly Val Gln Gln Glu Gly Ala Gln Gln Pro Gly Gly Gly
 1               5                  10                  15

Met Lys Lys Asp Asp Gln Ile Ala Ala Ala Ile Ala Leu Arg Gly Met
            20                  25                  30

Ala Gly Gly Gly Ser Asp Leu Arg Pro Lys Ser Ser Leu
        35                  40                  45

<210> SEQ ID NO 34
<211> LENGTH: 46
<212> TYPE: PRT
<213> ORGANISM: Borrelia sp.

<400> SEQUENCE: 34

Val Gln Glu Gly Val Gln Gln Glu Gly Ala Gln Gln Pro Gly Gly Gly
 1               5                  10                  15

Met Lys Lys Asp Asp Gln Ile Ala Ala Ala Ile Ala Leu Arg Gly Met
            20                  25                  30

Ala Gly Gly Gly Ile Arg Leu Ser Asn Arg Tyr Gln Ser Tyr
        35                  40                  45

<210> SEQ ID NO 35
<211> LENGTH: 47
```

```
<212> TYPE: PRT
<213> ORGANISM: Borrelia sp.

<400> SEQUENCE: 35

Val Gln Glu Gly Val Gln Gln Glu Gly Ala Gln Gln Pro Gly Gly Gly
 1               5                  10                  15

Met Lys Lys Asp Asp Gln Ile Ala Ala Ala Ile Ala Leu Arg Gly Met
            20                  25                  30

Ala Gly Gly Gly Tyr Leu Asp Glu Asp Asp Glu Asp Glu Tyr
        35                  40                  45

<210> SEQ ID NO 36
<211> LENGTH: 37
<212> TYPE: PRT
<213> ORGANISM: Borrelia sp.

<400> SEQUENCE: 36

Tyr Leu Asp Glu Asp Asp Glu Asp Asp Glu Tyr Tyr Glu Asp Asp Tyr
 1               5                  10                  15

Glu Gly Gly Gly Met Lys Lys Asp Asp Gln Ile Ala Ala Ala Ile Ala
            20                  25                  30

Leu Arg Gly Met Ala
        35

<210> SEQ ID NO 37
<211> LENGTH: 46
<212> TYPE: PRT
<213> ORGANISM: Borrelia sp.

<400> SEQUENCE: 37

Pro Val Val Ala Glu Ser Pro Lys Lys Pro Gly Gly Gly Val Gln Glu
 1               5                  10                  15

Gly Val Gln Gln Glu Gly Ala Gln Gln Pro Gly Gly Gly Met Lys Lys
            20                  25                  30

Asp Asp Gln Ile Ala Ala Ala Ile Ala Leu Arg Gly Met Ala
        35                  40                  45

<210> SEQ ID NO 38
<211> LENGTH: 46
<212> TYPE: PRT
<213> ORGANISM: Borrelia sp.

<400> SEQUENCE: 38

Val Gln Glu Gly Val Gln Gln Glu Gly Ala Gln Gln Pro Gly Gly Gly
 1               5                  10                  15

Pro Val Val Ala Glu Ser Pro Lys Lys Pro Gly Gly Gly Met Lys Lys
            20                  25                  30

Asp Asp Gln Ile Ala Ala Ala Ile Ala Leu Arg Gly Met Ala
        35                  40                  45

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asp, Asn, Ser or Arg
<220> FEATURE:
<221> NAME/KEY: MOD_RES
```

```
<222> LOCATION: (6)..(6)
<223> OTHER INFORMATION: Gln or Lys
<220> FEATURE:
<221> NAME/KEY: MOD_RES
<222> LOCATION: (8)..(8)
<223> OTHER INFORMATION: Ala, Gly or Val
<220> FEATURE:
<221> NAME/KEY: MOD_RES
<222> LOCATION: (11)..(11)
<223> OTHER INFORMATION: Met or Ile
<220> FEATURE:
<221> NAME/KEY: MOD_RES
<222> LOCATION: (12)..(12)
<223> OTHER INFORMATION: Ala or Val
<220> FEATURE:
<221> NAME/KEY: MOD_RES
<222> LOCATION: (16)..(16)
<223> OTHER INFORMATION: Met or Val
<220> FEATURE:
<221> NAME/KEY: MOD_RES
<222> LOCATION: (17)..(17)
<223> OTHER INFORMATION: Ala, Gly or Val

<400> SEQUENCE: 39

Met Lys Lys Xaa Asp Xaa Ile Xaa Ala Ala Xaa Xaa Leu Arg Gly Xaa
 1               5                  10                  15

Xaa

<210> SEQ ID NO 40
<211> LENGTH: 17
<212> TYPE: PRT
<213> ORGANISM: Borrelia sp.

<400> SEQUENCE: 40

Met Lys Lys Asn Asp Gln Ile Ala Ala Ala Ile Val Leu Arg Gly Met
 1               5                  10                  15

Ala

<210> SEQ ID NO 41
<211> LENGTH: 18
<212> TYPE: PRT
<213> ORGANISM: Borrelia afzelii

<400> SEQUENCE: 41

Met Lys Lys Arg Asn Asp Asn Ile Ala Ala Ala Ile Val Leu Arg Gly
 1               5                  10                  15

Val Ala

<210> SEQ ID NO 42
<211> LENGTH: 17
<212> TYPE: PRT
<213> ORGANISM: Borrelia sp.

<400> SEQUENCE: 42

Met Lys Lys Asn Asp Lys Ile Ala Ala Ala Ile Ala Leu Arg Gly Met
 1               5                  10                  15

Val

<210> SEQ ID NO 43
<211> LENGTH: 17
<212> TYPE: PRT
<213> ORGANISM: Borrelia sp.

<400> SEQUENCE: 43

Met Lys Lys Asn Asp Lys Ile Val Ala Ala Ile Ala Leu Arg Gly Met
 1               5                  10                  15
```

-continued

Val

<210> SEQ ID NO 44
<211> LENGTH: 17
<212> TYPE: PRT
<213> ORGANISM: Borrelia sp.

<400> SEQUENCE: 44

Met Lys Lys Asn Asp Lys Ile Ala Ala Ala Ile Val Leu Arg Gly Val
1               5                   10                  15

Ala

<210> SEQ ID NO 45
<211> LENGTH: 17
<212> TYPE: PRT
<213> ORGANISM: Borrelia sp.

<400> SEQUENCE: 45

Met Lys Lys Asn Asp Gln Ile Val Ala Ala Ile Ala Leu Arg Gly Met
1               5                   10                  15

Val

<210> SEQ ID NO 46
<211> LENGTH: 17
<212> TYPE: PRT
<213> ORGANISM: Borrelia sp.

<400> SEQUENCE: 46

Met Lys Lys Asn Asp Lys Ile Ala Ala Ala Ile Ala Leu Arg Gly Met
1               5                   10                  15

Gly

<210> SEQ ID NO 47
<211> LENGTH: 17
<212> TYPE: PRT
<213> ORGANISM: Borrelia sp.

<400> SEQUENCE: 47

Met Lys Lys Asn Asp Gln Ile Gly Ala Ala Ile Ala Leu Arg Gly Met
1               5                   10                  15

Val

<210> SEQ ID NO 48
<211> LENGTH: 17
<212> TYPE: PRT
<213> ORGANISM: Borrelia sp.

<400> SEQUENCE: 48

Met Lys Lys Asn Asp Gln Ile Gly Ala Ala Ile Ala Leu Arg Gly Met
1               5                   10                  15

Gly

<210> SEQ ID NO 49
<211> LENGTH: 7
<212> TYPE: PRT
<213> ORGANISM: Borrelia burgdorferi

<400> SEQUENCE: 49

Lys Asp Gly Lys Phe Ala Val
1               5

```
<210> SEQ ID NO 50
<211> LENGTH: 9
<212> TYPE: PRT
<213> ORGANISM: Borrelia garinii

<400> SEQUENCE: 50

Lys Asp Gly Gln Phe Ala Leu Lys Asp
 1               5

<210> SEQ ID NO 51
<211> LENGTH: 18
<212> TYPE: PRT
<213> ORGANISM: Borrelia garinii

<400> SEQUENCE: 51

Cys Met Lys Lys Asp Asp Gln Ile Ala Ala Ala Met Val Leu Arg Gly
 1               5                  10                  15

Met Ala

<210> SEQ ID NO 52
<211> LENGTH: 19
<212> TYPE: PRT
<213> ORGANISM: Borrelia afzelii

<400> SEQUENCE: 52

Cys Met Lys Lys Arg Asn Asp Asn Ile Ala Ala Ala Ile Val Leu Arg
 1               5                  10                  15

Gly Val Ala

<210> SEQ ID NO 53
<211> LENGTH: 18
<212> TYPE: PRT
<213> ORGANISM: Borrelia sp.

<400> SEQUENCE: 53

Cys Met Lys Lys Asn Asp Lys Ile Ala Ala Ala Ile Ala Leu Arg Gly
 1               5                  10                  15

Met Val

<210> SEQ ID NO 54
<211> LENGTH: 18
<212> TYPE: PRT
<213> ORGANISM: Borrelia sp.

<400> SEQUENCE: 54

Cys Met Lys Lys Asn Asp Lys Ile Ala Ala Ala Ile Val Leu Arg Gly
 1               5                  10                  15

Val Ala

<210> SEQ ID NO 55
<211> LENGTH: 18
<212> TYPE: PRT
<213> ORGANISM: Borrelia sp.

<400> SEQUENCE: 55

Cys Met Lys Lys Asn Asp Gln Ile Val Ala Ala Ile Ala Leu Arg Gly
 1               5                  10                  15

Met Val

<210> SEQ ID NO 56
<211> LENGTH: 18
```

```
<212> TYPE: PRT
<213> ORGANISM: Borrelia sp.

<400> SEQUENCE: 56

Cys Met Lys Lys Asn Asp Lys Ile Ala Ala Ala Ile Ala Leu Arg Gly
 1               5                  10                  15

Met Gly

<210> SEQ ID NO 57
<211> LENGTH: 18
<212> TYPE: PRT
<213> ORGANISM: Borrelia sp.

<400> SEQUENCE: 57

Cys Met Lys Lys Asn Asp Gln Ile Gly Ala Ala Ile Ala Leu Arg Gly
 1               5                  10                  15

Met Val

<210> SEQ ID NO 58
<211> LENGTH: 18
<212> TYPE: PRT
<213> ORGANISM: Borrelia sp.

<400> SEQUENCE: 58

Cys Met Lys Lys Asn Asp Gln Ile Gly Ala Ala Ile Ala Leu Arg Gly
 1               5                  10                  15

Met Gly

<210> SEQ ID NO 59
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Val Gln Glu Gly Val Gln Gln Glu Gly Ala Gln Gln Pro Gly Gly Gly
 1               5                  10                  15

Met Lys Lys Asn Asp Lys Ile Ala Ala Ala Ile Ala Leu Arg Gly Met
             20                  25                  30

Gly Gly Gly Gly Pro Val Val Ala Glu Ser Pro Lys Lys Pro
         35                  40                  45

<210> SEQ ID NO 60
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Cys Val Gln Glu Gly Val Gln Gln Glu Gly Ala Gln Gln Pro Gly Gly
 1               5                  10                  15

Gly Met Lys Lys Asn Asp Lys Ile Ala Ala Ala Ile Ala Leu Arg Gly
             20                  25                  30

Met Gly Gly Gly Gly Pro Val Val Ala Glu Ser Pro Lys Lys Pro
         35                  40                  45

<210> SEQ ID NO 61
<211> LENGTH: 46
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Val Gln Glu Gly Val Gln Gln Glu Gly Ala Gln Gln Pro Gly Gly Gly
1               5                   10                  15

Met Lys Lys Asn Asp Gln Ile Gly Ala Ala Ile Ala Leu Arg Gly Met
            20                  25                  30

Val Gly Gly Gly Pro Val Val Ala Glu Ser Pro Lys Lys Pro
        35                  40                  45

<210> SEQ ID NO 62
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Val Gln Glu Gly Val Gln Gln Glu Gly Ala Gln Gln Pro Gly Gly Gly
1               5                   10                  15

Met Lys Lys Asn Asp Lys Ile Ala Ala Ala Ile Val Leu Arg Gly Val
            20                  25                  30

Ala Gly Gly Gly Pro Val Val Ala Glu Ser Pro Lys Lys Pro
        35                  40                  45

<210> SEQ ID NO 63
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Val Gln Glu Gly Val Gln Gln Glu Gly Ala Gln Gln Pro Gly Gly Gly
1               5                   10                  15

Gly Gly Met Lys Lys Asn Asp Gln Ile Val Ala Ala Ile Ala Leu Arg
            20                  25                  30

Gly Met Val Gly Pro Val Val Ala Glu Ser Pro Lys Lys Pro
        35                  40                  45

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Val or Gly

<400> SEQUENCE: 64

Met Lys Lys Asn Asp Gln Ile Xaa Ala Ala Ile Ala Leu Arg Gly Val
1               5                   10                  15

Ala

<210> SEQ ID NO 65
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Lys Lys Asn Asp Gln Ile Val Ala Ala Ile Ala Leu Arg Gly Val
1               5                   10                  15

Ala

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Met Lys Lys Asn Asp Gln Ile Gly Ala Ala Ile Ala Leu Arg Gly Val
1               5                   10                  15

Ala

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Gln or Lys
<220> FEATURE:
<221> NAME/KEY: MOD_RES
<222> LOCATION: (8)..(8)
<223> OTHER INFORMATION: Val or Gly
<220> FEATURE:
<221> NAME/KEY: MOD_RES
<222> LOCATION: (11)..(11)
<223> OTHER INFORMATION: Met or Ile
<220> FEATURE:
<221> NAME/KEY: MOD_RES
<222> LOCATION: (12)..(12)
<223> OTHER INFORMATION: Val or Ala
<220> FEATURE:
<221> NAME/KEY: MOD_RES
<222> LOCATION: (17)..(17)
<223> OTHER INFORMATION: Ala, Gly or Val

<400> SEQUENCE: 67

Met Lys Lys Asn Asp Xaa Ile Xaa Ala Ala Xaa Xaa Leu Arg Gly Val
1               5                   10                  15

Xaa

<210> SEQ ID NO 68
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Val or Gly
```

```
<400> SEQUENCE: 68

Val Gln Glu Gly Val Gln Gln Glu Gly Ala Gln Gln Pro Gly Gly Gly
 1               5                  10                  15

Met Lys Lys Asn Asp Gln Ile Xaa Ala Ala Ile Ala Leu Arg Gly Val
            20                  25                  30

Ala

<210> SEQ ID NO 69
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Gln Glu Gly Val Gln Gln Glu Gly Ala Gln Gln Pro Gly Gly Gly
 1               5                  10                  15

Met Lys Lys Asn Asp Gln Ile Val Ala Ala Ile Ala Leu Arg Gly Val
            20                  25                  30

Ala

<210> SEQ ID NO 70
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys Val Gln Glu Gly Val Gln Gln Glu Gly Ala Gln Gln Pro Gly Gly
 1               5                  10                  15

Gly Met Lys Lys Asn Asp Gln Ile Val Ala Ala Ile Ala Leu Arg Gly
            20                  25                  30

Val Ala

<210> SEQ ID NO 71
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Val Gln Glu Gly Val Gln Gln Glu Gly Ala Gln Gln Pro Gly Gly Gly
 1               5                  10                  15

Met Lys Lys Asn Asp Gln Ile Gly Ala Ala Ile Ala Leu Arg Gly Val
            20                  25                  30

Ala

<210> SEQ ID NO 72
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Val Gln Glu Gly Val Gln Gln Glu Gly Ala Gln Gln Pro Gly Gly
```

```
                1               5                  10                 15
Gly Met Lys Lys Asn Asp Gln Ile Gly Ala Ala Ile Ala Leu Arg Gly
                   20                 25                 30

Val Ala

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Val or Gly

<400> SEQUENCE: 73

Met Lys Lys Asn Asp Gln Ile Xaa Ala Ala Ile Ala Leu Arg Gly Val
  1               5                  10                 15

Ala Lys

<210> SEQ ID NO 74
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Val or Gly

<400> SEQUENCE: 74

Met Lys Lys Asn Asp Gln Ile Xaa Ala Ala Ile Ala Leu Arg Gly Val
  1               5                  10                 15

Ala Lys Asp

<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Val or Gly

<400> SEQUENCE: 75

Met Lys Lys Asn Asp Gln Ile Xaa Ala Ala Ile Ala Leu Arg Gly Val
  1               5                  10                 15

Ala Lys Asp Gly
            20

<210> SEQ ID NO 76
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
```

```
<223> OTHER INFORMATION: Val or Gly

<400> SEQUENCE: 76

Met Lys Lys Asn Asp Gln Ile Xaa Ala Ala Ile Ala Leu Arg Gly Val
 1               5                  10                  15

Ala Lys Asp Gly Lys
            20

<210> SEQ ID NO 77
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Val or Gly

<400> SEQUENCE: 77

Met Lys Lys Asn Asp Gln Ile Xaa Ala Ala Ile Ala Leu Arg Gly Val
 1               5                  10                  15

Ala Lys Asp Gly Lys Phe
            20

<210> SEQ ID NO 78
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Val or Gly

<400> SEQUENCE: 78

Met Lys Lys Asn Asp Gln Ile Xaa Ala Ala Ile Ala Leu Arg Gly Val
 1               5                  10                  15

Ala Lys Asp Gly Lys Phe Ala
            20

<210> SEQ ID NO 79
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Val or Gly

<400> SEQUENCE: 79

Met Lys Lys Asn Asp Gln Ile Xaa Ala Ala Ile Ala Leu Arg Gly Val
 1               5                  10                  15

Ala Lys Asp Gly Lys Phe Ala Val
            20

<210> SEQ ID NO 80
<211> LENGTH: 18
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 80

Cys Met Lys Lys Asn Asp Gln Ile Val Ala Ala Ile Ala Leu Arg Gly
 1               5                  10                  15

Val Ala

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Met Lys Lys Asn Asp Gln Ile Gly Ala Ala Ile Ala Leu Arg Gly
 1               5                  10                  15

Val Ala
```